United States Patent
Wang et al.

(10) Patent No.: US 9,562,229 B2
(45) Date of Patent: Feb. 7, 2017

(54) METHODS FOR INCLUDING CARDIOMYOCYTE PROLIFERATION

(71) Applicant: Children's Medical Center Corporation, Boston, MA (US)

(72) Inventors: Da-Zhi Wang, Newton, MA (US); Jinghai Chen, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/766,505

(22) PCT Filed: Feb. 6, 2014

(86) PCT No.: PCT/US2014/015132
§ 371 (c)(1),
(2) Date: Aug. 7, 2015

(87) PCT Pub. No.: WO2014/124155
PCT Pub. Date: Aug. 14, 2014

(65) Prior Publication Data
US 2016/0024501 A1    Jan. 28, 2016

Related U.S. Application Data

(63) Continuation of application No. 13/828,208, filed on Mar. 14, 2013, now abandoned.

(60) Provisional application No. 61/762,240, filed on Feb. 7, 2013.

(51) Int. Cl.
| *A61P 9/10* | (2006.01) |
| *A61P 9/00* | (2006.01) |
| *C12N 15/113* | (2010.01) |
| *A61K 31/713* | (2006.01) |

(52) U.S. Cl.
CPC ........... *C12N 15/113* (2013.01); *A61K 31/713* (2013.01); *C12N 2310/141* (2013.01); *C12N 2310/3515* (2013.01); *C12N 2320/30* (2013.01); *C12N 2320/32* (2013.01); *C12N 2330/51* (2013.01)

(58) Field of Classification Search
None
See application file for complete search history.

(56) References Cited

U.S. PATENT DOCUMENTS

| 2009/0306181 A1 | 12/2009 | Ikeda et al. |
| 2010/0273856 A1 | 10/2010 | Smith et al. |
| 2011/0086348 A1 | 4/2011 | Prasad et al. |

FOREIGN PATENT DOCUMENTS

| WO | WO 2010/033773 | 3/2010 |
| WO | 2012/112832 | 8/2012 |
| WO | WO 2013/057527 | 4/2013 |

OTHER PUBLICATIONS

International Preliminary Report on Patentability for PCT/US2014/015132 dated Sep. 15, 2015.
International Search Report and Written Opinion for PCT/US2014/015132 dated Apr. 15, 2015.
Ahuja et al., "Cardiac myocyte cell cycle control in development, disease, and regeneration," Physiol Rev., 2007, 87(2):521-544.
Bersell et al. "Neuregulin1/ErbB4 signaling induces cardiomyocyte proliferation and repair of heart injury", Cell, Jul. 24, 2009, 138(2):257-270.
Bonauer et al., "MicroRNA-92a controls angiogenesis and functional recovery of ischemic tissues in mice," Science, 2009, 324(5935):1710-1713.
Callis et al., "MicroRNA-208a is a regulator of cardiac hypertrophy and conduction in mice," J Clin Invest., 2009, 119(9):2772-2786.
Conkrite et al., "miR-17~92 cooperates with RB pathway mutations to promote retinoblastoma," Genes Dev., 2011, 25(16):1734-1745.
Crackower et al., "Regulation of myocardial contractility and cell size by distinct PI3K-PTEN signaling pathways," Cell, 2002, 110(6):737-749.
Danielson et al., "Cardiovascular dysregulation of miR-17-92 causes a lethal hypertrophic cardiomyopathy and Arrhythmogenesis," FASEB J., 2013, 27:1-8.
de Pontual et al., "Germline deletion of the miR-17 approximately 92 cluster causes skeletal and growth defects in humans," Nat Genet., 2011, 43(10):1026-1030.
Elmen et al., "LNA-mediated microRNA silencing in non-human primates," Nature, 2008, 452:896-899.
Esau et al., "miR-122 regulation of lipid metabolism revealed by in vivo antisense targeting," Cell Metabolism, 2006, 3(2):87-98.
Frank et al., "MicroRNA-20a inhibits stress-induced cardiomyocyte apoptosis involving its novel target Egln3/PHD3," J Molecular Cell Cardiol., 2012, 52:711-717.
Hassink et al., "Cardiomyocyte cell cycle activation improves cardiac function after myocardial infarction," Cardiovasc Res., 2008, 78(1):18-25.
Hayashita et al., "A Polycistronic MicroRNA Cluster, miR-17-92, Is Overexpressed in Human Lung Cancers and Enhances Cell Proliferation," Cancer Res., 2005, 65:9628-9632.
He et al., "A microRNA polycistron as 833 a potential human oncogene," Nature, 2005, 435(7043):828-833.
Jopling et al., "Zebrafish heart regeneration occurs by cardiomyocyte dedifferentiation and proliferation," Nature, 2010, 464(7288):606-609.
Kasinski and Slack, "MicroRNAs en route to the clinic: progress in validating and targeting microRNAs for cancer therapy," Nat Rev Cancer, 2011, 11(12):849-864.
Kathiresan and Srivastava, "Genetics of human cardiovascular disease," Cell, 2012, 148(6):1242-1257.

(Continued)

*Primary Examiner* — Jennifer McDonald
(74) *Attorney, Agent, or Firm* — Fish & Richardson P.C.

(57) ABSTRACT

Methods for inducing cardiomyocyte proliferation, e.g., in vivo, by administering a composition comprising miRNA17-92 cluster oligonucleotides, e.g., miR-19a oligonucleotides, miR-19b oligonucleotides, or both miR-19a and miR-19b oligonucleotides.

28 Claims, 32 Drawing Sheets

(56) References Cited

OTHER PUBLICATIONS

Kikuchi et al., "Primary contribution to zebrafish heart regenemtion by gata4(+) cardiomyocytes," Nature, 2010, 464(7288):601-605.
Krützfeldt et al., "Silencing of microRNAs in vivo with 'antagomirs'," Nature, 2005, 438:685-689.
Lepilina et al., "A dynamic epicardial injury response supports progenitor cell activity during zebrafish heart regeneration," Cell, 2006, 127(3):607-619.
Meenhuis et al., "MiR-17/20/93/106 promote hematopoietic cell expansion by targeting sequestosome 1-regulated pathways in mice," Blood, 2011, 118:916-925.
Mendell, "miRiad Roles for the miR-17-92 Cluster in Development and Disease," Cell, Apr. 18, 2008, 133:217-222.
Mestdagh et al., "The miR-17-92 microRNA cluster regulates multiple components of the TGF-beta pathway in neuroblastoma," Mol Cell., 2010, 40(5):762-773.
Mudd and Kass, "Tackling heart failure in the twenty-first century," Nature, 2008, 451(7181):919-928.
O'Donnell et al., "c-Myc-regulated microRNAs modulate E2F1 expression," Nature, 2005, 435(7043):839-843.
Olive et al., "miR-19 is a key oncogenic component of mir-17-92," Genes Dev., 2009, 23(24):2839-2849.
Pasumarthi et al., "Targeted expression of cyclin D2 results in cardiomyocyte DNA synthesis and infarct regression in transgenic mice," Circ Res., 2005, 96(1):110-118.
Pfeffer et al., "Progressive ventricular remodeling in rat with myocardial infarction," Am J Physiol., 1991, 260:H1406-1414.
Porrello et al., "Transient regenerative potential of the neonatal mouse heart," Science, 2011, 331(6020):1078-1080.
Poss et al., "Heart regeneration in zebrafish," Science, 2002, 298(5601):2188-2190.
Rubart and Field, "Cardiac regeneration: repopulating the heart," Annu Rev Physiol., 2006, 68:29-49.
Shan et al., "MicroRNA MiR-17 retards tissue growth and represses fibronectin expression," Nat Cell Biol., 2009, 11(8):1031-1038.
Sirish et al., "MicroRNA profiling predicts a variance in the proliferative potential of cardiac progenitor cells derived from neonatal and adult murine hearts," J Molecular Cell. Cardiol., 2012, 52:264-272.
Soonpaa et al., "Cyclin D1 overexpression promotes cardiomyocyte DNA synthesis and multinucleation in transgenic mice," J Clin Invest., 1997, 99(11):2644-2654.
Sun et al., "Sustained axon regeneration induced by co-deletion of PTEN and SOCS3," Nature, 2011, 480(7377):372-375.
Tatsuguchi et al., "Expression of microRNAs is dynamically regulated during cardiomyocyte hypertrophy," J Mol Cell Cardiol., 2007, 42(6):1137-1141.
Trompeter et al., "MicroRNAs MiR-17, MiR-20a, and MiR-106b Act in Concert to Modulate E2F Activity on Cell Cycle Arrest during Neuronal Lineage Differentiation of USSC," PLoS One, 2011, 6(1):e16138, 1-13.
Ventura et al., "Targeted deletion reveals essential and overlapping functions of the miR-17~92 family of miRNA clusters," Cell, 2008, 132:875-886.
Volinia et al., "A microRNA expression signature of human solid tumors defines cancer gene targets," Proc Natl Acad Sci U S A, 2006, 103(7):2257-2261.
Warren et al., "Highly efficient reprogramming to pluripotency and directed differentiation of human cells with synthetic modified mRNA," Cell Stem Cell, 2010, 7(5):618-630.
Xiang et al., "The miR-17-92 cluster regulates FOG-2 expression and inhibits proliferation of mouse embryonic cardiomyocytes," Brazilian J Med. Biol. Res., 2012, 45:131-138.
Xiao et al., "Lymphoproliferative disease and autoimmunity in mice with increased miR-17-92 expression in lymphocytes," Nat Immunol., 2008, 9(4):405-414.
Leor et al., "Cardiogenic shock complicating acute myocardial infarction in patients without heart failure on admission: incidence, risk factors, and outcome. Sprint Study Group," Am J Med. 94(3):265-73, 1993.
Jousilahti et al., "Parental history of premature coronary heart disease: an independent risk factor of myocardial infarction," J Clin Epidemiol. May 1996; 49(5):497-503.
Kannel, "Current status of the epidemiology of heart failure," Curr Cardiol Rep. May 1999; 1(1):11-9.
Kannel and Cupples, "Epidemiology and risk profile of cardiac failure," Cardiovascular Drugs and Therapy 2(1): Supplement, pp. 387-395, 1988.
Khawaja et al., "Usefulness of desirable lifestyle factors to attenuate the risk of heart failure among offspring whose parents had myocardial infarction before age 55 years," Am J Cardiol. Aug. 1, 2012; 110(3):326-30.
Kannel, "Incidence and Epidemiology of Heart Failure," Heart Failure Reviews, 5:167-173, 2000.
Gražulevičienė and Dulskienė "Risk factors for heart failure in survivors after first myocardial infarction," 2006; Medicina (Kaunas) 42(10):810-816.
O'Leary et al., "Carotid-artery intima and media thickness as a risk factor for myocardial infarction and stroke in older adults. Cardiovascular Health Study Collaborative Research Group," N. Engl J Med. Jan. 7, 1999; 340(1):14-22.
Kannel, "Hazards, risks, and threats of heart disease from the early stages to symptomatic coronary heart disease and cardiac failure," Cardiovasc Drugs Ther. May 1997; 11 Suppl 1:199-212.
Mozaffarian et al., "Beyond established and novel risk factors: lifestyle risk factors for cardiovascular disease," Circulation. Jun. 10, 2008; 117(23):3031-8.
Wright, et al., "In vivo myocardial gene transfer: optimization, evalutation and direct comparison of gene transfer vectors," Basic Res. Cardiol. 96, 227-236, 2001.
Zincarelli et al., "Analysis of AAV serotypes 1-9 mediated gene expression and tropism in mice after systemic injection," Mol Ther 16, 1073-1080, 2008.

| | Mean cell area (μm²) | Long axis (μm) | Short axis (μm) |
|---|---|---|---|
| miR-17-92$^{flox/flox}$ | 2920±109 | 123.8±3.6 | 29.2±1.2 |
| miR-17-92$^{flox/flox}$; Nkx2.5-Cre | 3922±132 ** | 129.3±2.9 | 34.5±1.1 ** |

| Genotypes | miR17-92$^{fl/+}$ | miR17-92$^{fl/+}$; Nkx-Cre | miR17-92$^{fl/fl}$ | miR17-92$^{fl/fl}$; Nkx-Cre | Total |
|---|---|---|---|---|---|
| Number | 84 | 94 | 97 | 70 | 345 |
| Percentage | 24.4% | 27.2% | 28.1% | 20.3% | 100% |

FIG. 2D                    FIG. 2E

| Genotypes | miR17-92^{TG/+} | miR17-92^{TG/+}; Nkx-Cre | miR17-92^{TG/TG} | miR17-92^{TG/TG}; Nkx-Cre | Total |
|---|---|---|---|---|---|
| Number | 48 | 39 | 32 | 27 | 146 |
| Percentage | 32.9% | 26.7% | 21.9% | 18.5% | 100% |

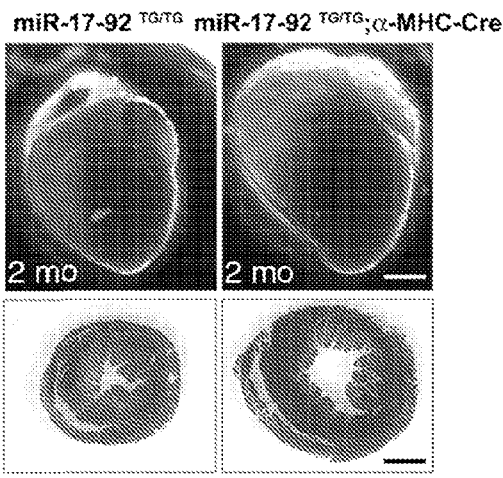
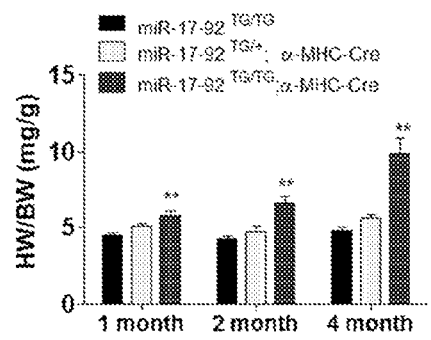
FIG. 3A
FIG. 3B
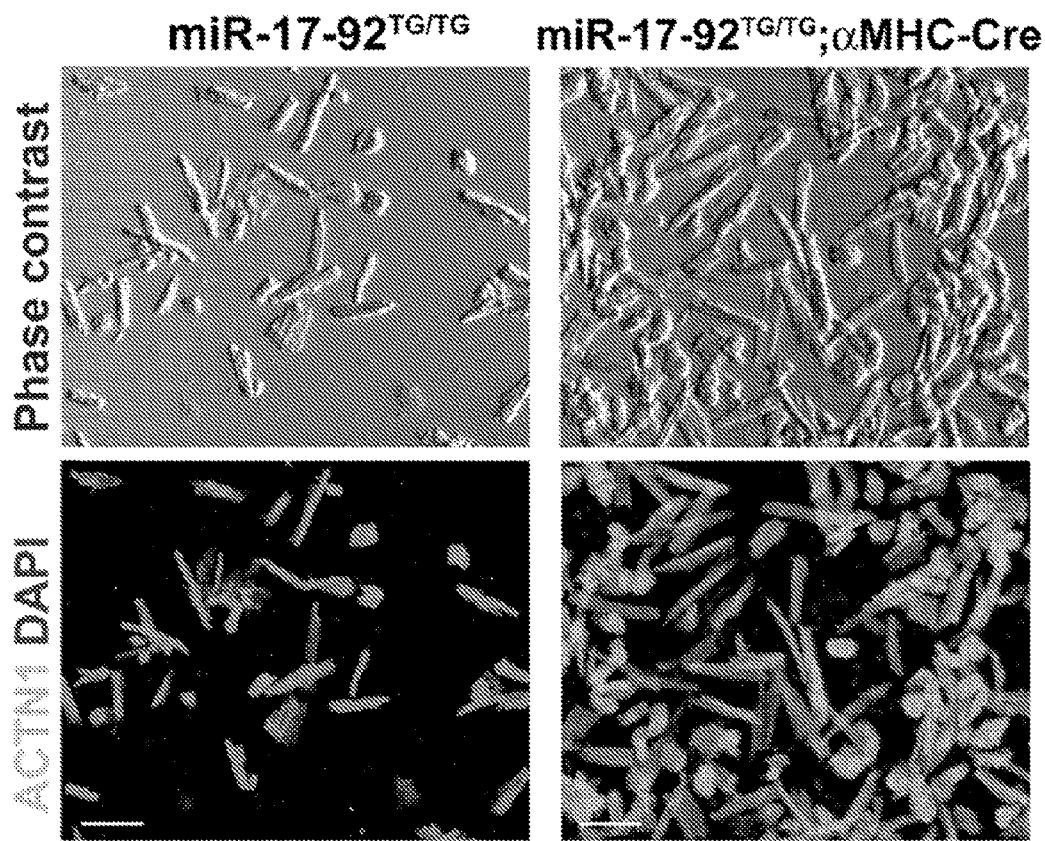
FIG. 3C

FIG. 3D
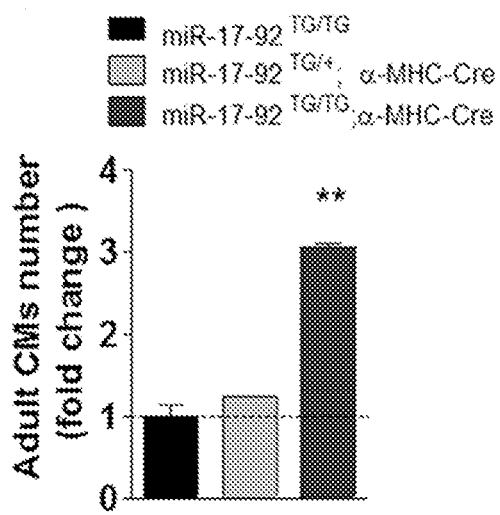
FIG. 3E
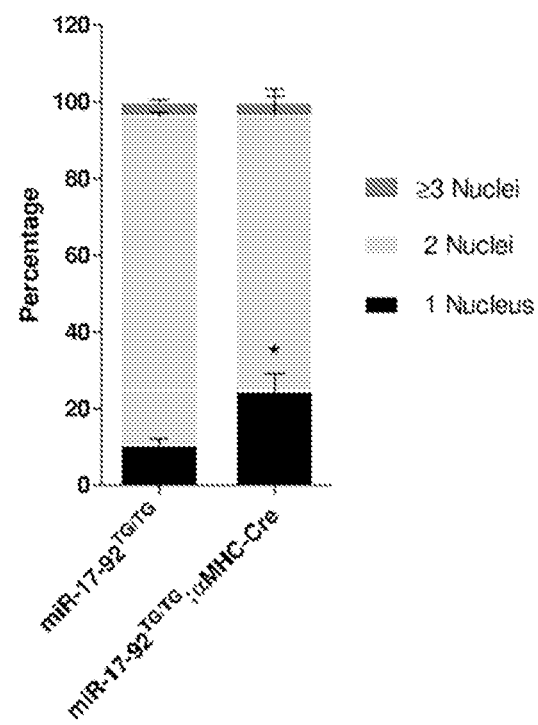
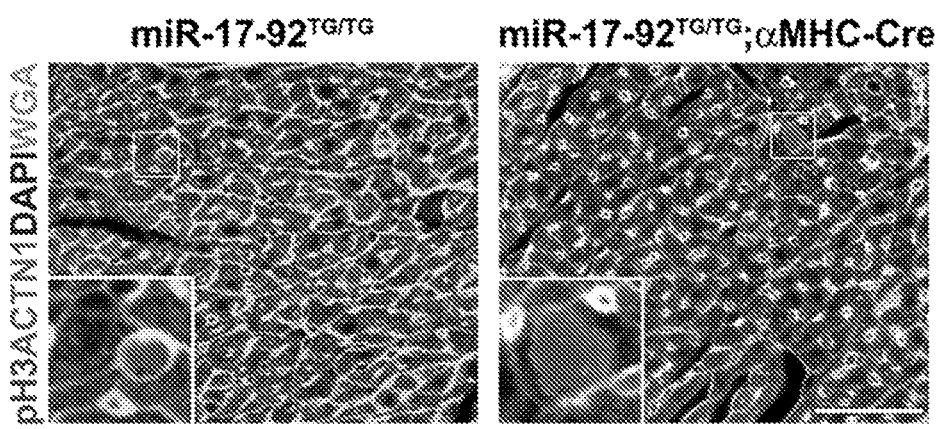
FIG. 3F

FIG. 3G
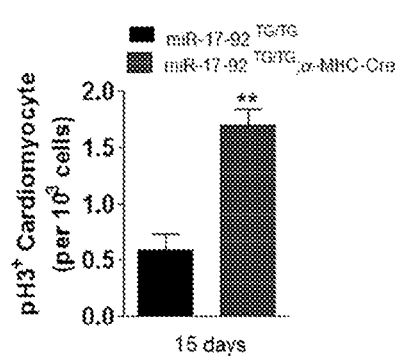
FIG. 3H
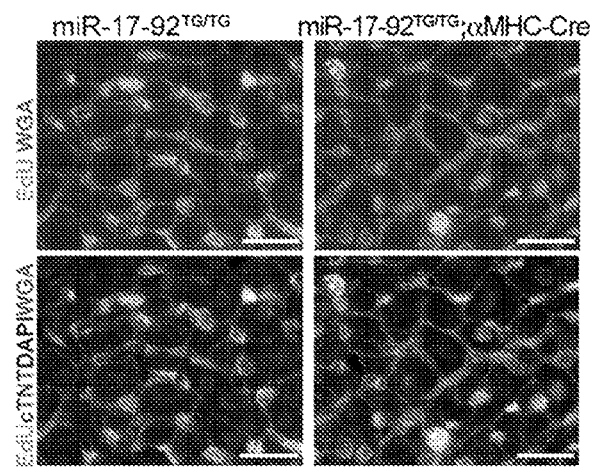
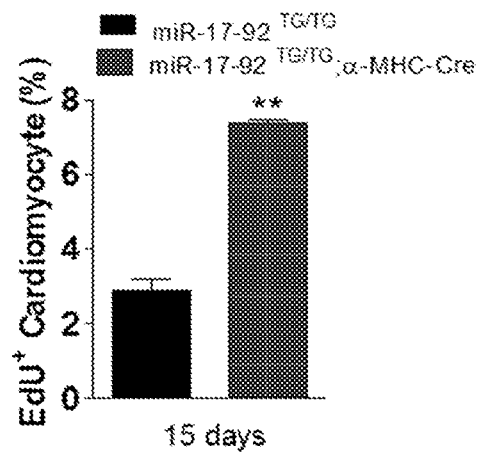
FIG. 3I

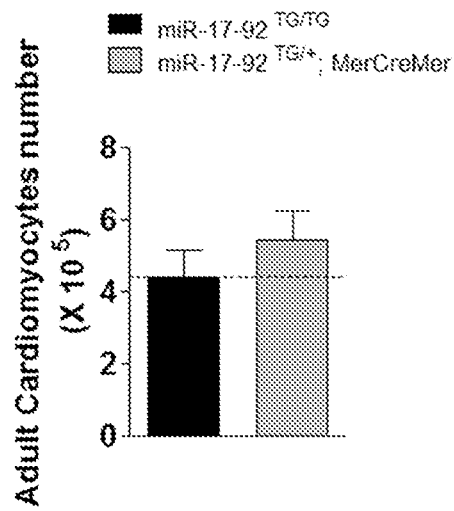
FIG. 4C
| | Mean cell area (μm²) | Long axis (μm) | Short axis (μm) |
|---|---|---|---|
| miR-17-92$^{TG/TG}$ | 5898±247 | 153.3±4.1 | 49.5±1.9 |
| miR-17-92$^{TG/TG}$; MerCreMer | 5158±260 * | 163.2±4.5 | 42.7±1.5 ** |
FIG. 4D
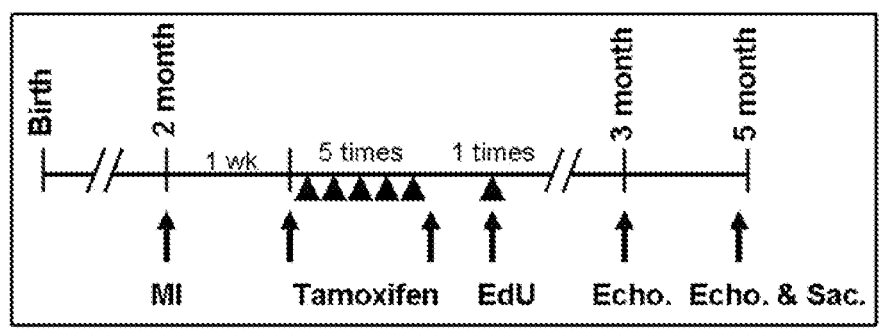
FIG. 4E

```
    u   u                        --      ---      ag
gcag  cc  cuguuaguuuugcauag   uugcac   uaca    a
||||  ||  ||||||||||||||||||  ||||||   ||||    a
cguc  gg  gguagucaaaacguauc   aacgug   augu    g
    c   u                        ua      uug     aa
```

```
    uu                     -  -     uc       ugugu
cacug   cuaugguuaguuuugca  gg  uuugca   cagc         g
|||||   ||||||||||||||||| ||  ||||||   ||||          a
gugau   ggugucagucaaaacgu  cc  aacgu    gucg         u
  --                        a  u         --      ucuua
```

```
    cuac                        -  -       uuca         u
acauug      uuacaauuaguuuugca  gg  uuugcau      gcguaua  a
||||||      ||||||||||||||||| ||  ||||||||      |||||||
uguaau      agaguuagucaaaacgu  cc  aaacgug      uguauau  u
  ----                          a  u             ucgg       g
```

METHODS FOR INCLUDING CARDIOMYOCYTE PROLIFERATION

CLAIM OF PRIORITY

This application is a 371 U.S. National of PCT Application No.: PCT/US2014/015132, filed Feb. 6, 2014, which claims the benefit of U.S. Provisional Patent Application No. 61/762,240, filed on Feb. 7, 2013, and U.S. Utility patent application Ser. No. 13/828,208, filed Mar. 14, 2013. The entire contents of the foregoing are incorporated by reference herein.

FEDERALLY SPONSORED RESEARCH OR DEVELOPMENT

This invention was made with Government support under Grant No. HL085635 awarded by the National Institutes of Health. The Government has certain rights in the invention.

TECHNICAL FIELD

This invention relates to methods for inducing cardiomyocyte proliferation, e.g., in vivo, by administering a composition comprising a microRNA (miRNA)-17-92 cluster miRNA, e.g., miR-17, miR-18a, miR-19a, miR-20a, miR-19b-1, and miR-92a-1, preferably miR-19a and/or miR-19b, or both.

BACKGROUND

Cardiomyocytes in adult mammalian hearts are terminally differentiated cells that have exited from the cell cycle and lost most of their proliferative capacity. Death of mature cardiomyocytes in pathological cardiac conditions and the lack of regenerative capacity of adult hearts are primary causes of heart failure and mortality.

SUMMARY

At least in part, the present invention is based on the discovery that members of miR-17-92 cluster, and miR-19a/b in particular, are required for and sufficient to induce cardiomyocyte proliferation in vitro and in vivo. PTEN, a tumor suppressor, was identified as a miR-17-92 target to mediate the function of miR-17-92 in cardiomyocyte proliferation. The present studies therefore identify miR-17-92 as a critical regulator of cardiomyocyte proliferation and support the use of this cluster of miRNAs as therapeutic targets for cardiac repair and heart regeneration.

Thus, in a first aspect, the invention provides methods for treating, or reducing the risk of developing, a myocardial infarction or chronic heart failure in a subject. The methods include identifying a subject in need of treatment for a myocardial infarction or chronic heart failure; and administering to the subject a therapeutically effective amount of an microRNA (miR)-microRNA (miRNA)-17-92 cluster miRNA oligonucleotide, e.g., a miR-17, miR-18a, miR-19a, miR-20a, miR-19b-1, and miR-92-1 oligonucleotide, preferably a miR-19a and/or miR-19b oligonucleotide(s). Also provided is use of a microRNA (miRNA)-17-92 cluster miRNA oligonucleotide, e.g., a miR-17, miR-18a, miR-19a, miR-20a, miR-19b-1, and miR-92-1 oligonucleotide, preferably a miR-19a and/or miR-19b oligonucleotide(s), for treating, or reducing the risk of developing, a myocardial infarction or chronic heart failure in a subject In some embodiments, the subject is over the age of 65; does not yet have chronic heart failure; or has not yet had a myocardial infarction.

In some embodiments, the therapeutically effective amount is an amount sufficient to induce cardiomyocyte proliferation.

In some embodiments, the amount of cardiomyocyte proliferation is sufficient to improve cardiac function, increase cardiac contractile force, or increase the thickness of the myocardium; and wherein the method optionally includes detecting an improvement in cardiac function, an increase in cardiac contractile force, or an increase in the thickness of the myocardium.

In some embodiments, the oligonucleotide is a single stranded DNA or RNA that is at least 18, 19, or 20 nucleotides long, but less than 24, 25, 26, 27, 28, 29, or 30 nucleotides long, and is at least 80% identical to SEQ ID NOs:1, 3, 6, 8, 10 or 12, preferably SEQ ID NOs:1 or 3, with 100% identity to nucleotides 1-8 of SEQ ID NOs:1, 3, 6, 8, 10 or 12, preferably SEQ ID NOs:1 or 3, i.e., comprises the seed sequence as shown herein, plus 0 or 1 nucleotide on the 5' end, and/or 0, 1, 2, 3, 4, 5, 6, 7, 8, 9, 10, 11, 12, 13, or 14 nucleotides on the 3' end (up to the full length mature sequence).

In some embodiments, the oligonucleotide comprises at least one modification selected from the group consisting of: 5'-phosphorylation; at least one 2'-fluoro ribose modification; and a cholesterol moiety.

In some embodiments, the oligonucleotide comprises SEQ ID NOs:1, 3, 6, 8, 10 or 12, preferably SEQ ID NOs:1 or 3.

In some embodiments, the oligonucleotide is a double stranded DNA or RNA, comprising: a first strand comprising a sequence that is at least 80% identical to 18, 19, or 20 consecutive nucleotides of SEQ ID NOs:1, 3, 6, 8, 10 or 12, with 100% identity to nucleotides 1-8 of SEQ ID NOs:1, 3, 6, 8, 10 or 12; a second strand comprising a sequence that is complementary to the first strand; and an optional linker therebetween.

In some embodiments, the double stranded DNA or RNA comprises SEQ ID NO:2, 4, 5, 7, 9, 11, 13, or 14, preferably SEQ ID NOs:2 or 4.

In some embodiments, the double stranded DNA or RNA comprises at least one modification selected from the group consisting of: 5'-phosphorylation; and 2'-O-methyl ribosyl substitution at position 2 in the first strand, i.e., position 2 in the sequence corresponding to the mature miRNA.

In some embodiments, the oligonucleotide is administered locally to the heart of the subject.

In some embodiments, the oligonucleotide is administered using a virus, e.g., adenoassociated viruses (AAV), e.g., AAV9; a nanoparticle or microparticle delivery; or a gelfoam.

In some embodiments, the subject is a post-neonatal, adolescent, or adult mammal, e.g., human. As used herein, post-neonatal refers to a subject who is beyond the newborn stage, e.g., in humans at least 3, 4, 5, 6, 7, 8, 9, 10, 11 or 12 months old.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2a-h. miR-17-92 induces cardiomyocyte proliferation in embryonic and postnatal hearts
(a) Gross morphology of hearts of 3 weeks old control and miR-17-92-TG$^{nkx2.5}$ mice (upper panel, bar=1 mm) Haematoxylin and Eosin (H&E) staining of sagittal sections of 3 week old control and miR-17-92-TG$^{nkx2.5}$ mice (middle panel, bar=1 mm); higher magnification of ventricle myocardium (lower panel, bar=250 μm.)
(b) Immunohistochemistry of phosphorylated histone H3 (phospho-H3) on sagittal sections of embryonic 16.5 (E16.5) control and miR-17-92-TG$^{nkx2.5}$ hearts (upper panel, bar=500 μm); Immunohistochemistry of pH3 on sagittal sections of E16.5 wild type and miR-17-92-TG$^{nkx2.5}$ hearts, α-actinin (ACTN1) marks cardiomyocytes; DAPI labels nuclei (middle panel, bar=50 μm); white boxes are enlarged in lower panels (lower panel, bar=20 μm).
(c) Immunohistochemistry of phospho-H3 on sagittal sections of postnatal day 4 (P4) control and miR-17-92-TG$^{nkx2.5}$ hearts (upper panel, bar=500 μm); Immunohistochemistry of pH3 on sagittal sections of P4 control and miR-17-92-TG$^{nkx2.5}$ hearts, α-actinin (ACTN1) marks cardiomyocytes; DAPI labels nuclei (middle panel, bar=50 μm); white boxes are enlarged in lower panels (lower panel, bar=20 μm).
(d) Quantification of percentages of phosphorylated histone H3 (pH3$^+$) cardiomyocytes in E16.5 and P4 control and miR-17-92-TG$^{nkx2.5}$ hearts. N=3 for each group.
(e) The Heart Weight/Body Weight (HW/BW) ratio of 3-week-old miR-17-92 transgenic mice (miR-17-92$^{TG/TG}$; Nkx2-5$^{Cre/+}$) and their control littermates were shown. N of each genotype was indicated. *: P<0.05; **: P<0.01.
(f) Strategy of cardiac-specific overexpression of miR-17-92 cluster in vivo.
(g) Genotyping results of weaning age mice from intercrossing of miR-17-92$^{TG/TG}$ and miR-17-92$^{TG/+}$;Nkx2-5$^{Cre/+}$ mice.
(h) Increased expression of members of the miR-17-92 cluster in the hearts of miR-17-92 transgenic mice. The expression of members in miR-17-92 cluster in heart samples of miR-17-92$^{TG/TG}$, miR-17-92$^{TG/+}$;αMHC-Cre and miR-17-92$^{TG/TG}$;αMHC-Cre mice was determined by quantitative RT-PCR. N of each genotype was indicated.

FIGS. 3a-k. miR-17-92 induces cardiomyocyte proliferation in postnatal and adult hearts
(a) Gross morphology of hearts of 2 months old control and miR-17-92-TG$^{MHC}$ mice (upper panel). Haematoxylin and Eosin (H&E) staining of transverse sections of 2 months old control and miR-17-92-TG$^{MHC}$ hearts (lower panels). Bars=1 mm.
(b) Heart weight (HW) to body weight (BW) ratios of 1-, 2-, and 4-months old wild type, heterozygote and homozygote miR-17-92-TG$^{MHC}$ mice. N=5 for each group.
(c) Morphology of freshly isolated adult cardiomyocytes from hearts of miR-17-92-TG$^{MHC}$ and control mice. α-actinin (ACTN1) marks rod shaped cardiomyocytes (lower panel). Bars=250 μm.
(d) Quantification of total isolated adult cardiomyocytes from 2 months old hearts of miR-17-92-TG$^{MHC}$ and control mice. N=3 for each genetic group.

Figure 1A:
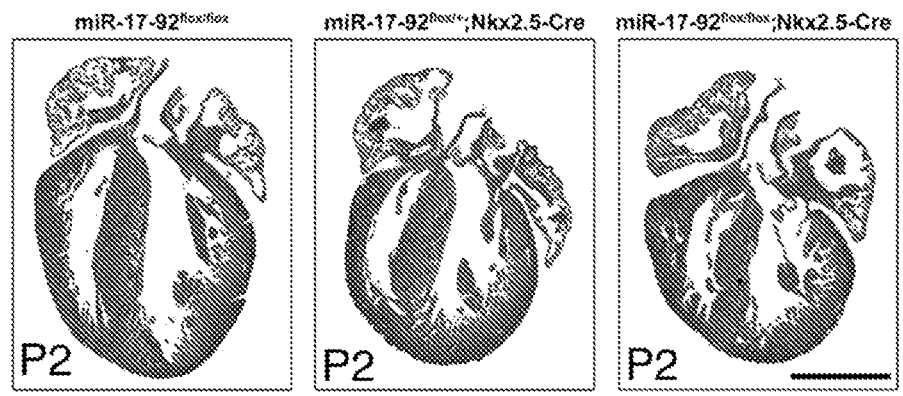
FIGS. 1a-n. miR-17-92 is Required for Cardiomyocyte Proliferation in Embryonic, Postnatal and Adult Hearts
(a) Haematoxylin and Eosin (H&E) staining of sagittal sections of hearts from 2 days old wild type, heterozygote and mutant miR-17-92-KO mice. Bar=1 mm.
(b) Immunohistochemistry of phosphorylated histone H3 (phospho-H3) on sagittal sections of hearts from 2 days old wild type, heterozygote and mutant miR-17-92-KO mice. Bar=100 μm.
(c) Immunohistochemistry of sagittal sections of hearts from 2 days old wild type, heterozygote and mutant miR-17-92-KO mice. White boxes are enlarged in lower panels. Phosphorylated histone H3 (pH3) labels proliferating cells; α-actinin (ACTN1) marks cardiomyocytes; DAPI labels nuclei. Bars=50 μm in upper panel and 20 μm in lower panel.
(d) Quantification of pH3 positive cardiomyocytes in wild type, heterozygote and mutant miR-17-92-KO hearts from 2 days old mice. **P<0.01 between genetic groups. (N=4~5 each group).
(e) Haematoxylin and Eosin (H&E) staining of transverse sections of hearts from 10 months old wild type, heterozygote and mutant miR-17-92-KO mice. Bar=1 mm.
(f) Heart weight (HW) to body weight (BW) ratios of 1 year old wild type, heterozygote and mutant miR-17-92-KO mice. N of each genotype group listed.
(g) Morphology of freshly isolated adult cardiomyocytes from hearts of miR-17-92-KO and control mice. α-actinin (ACTN1) marks rod shaped cardiomyocytes (lower panel). Bars=250 μm.
(h) Quantification of total isolated adult cardiomyocytes from hearts of miR-17-92-KO and control mice. N of each genotype group is listed.
(i) Quantitative measurement of the size of freshly isolated adult cardiomyocytes from hearts of miR-17-92-KO and control mice. One hundred individual cells from three different hearts were analyzed per group. **P<0.01 between genetic groups.
(j) Strategy of cardiac-specific knockout of mirR-17-92 cluster in vivo.
(k) Genotyping results of weaning age mice from intercrossing of mir-17-92$^{flox/flox}$ and miR-17-92$^{flox/+}$;Nkx2-5$^{Cre/+}$ mice.
(l) The expression of members of the miR-17-92 cluster in 3-week old heart samples of mir-17-92$^{flox/flox}$, miR-17-92$^{flox/+}$;Nkx2-5$^{Cre/+}$ and miR-17-92$^{flox/flox}$;Nkx2-5$^{Cre/+}$ mice was determined by quantitative RT-PCR. N of each genotype was indicated.
(m) Cross section area of cardiomyocyte in adult hearts of mir-17-92$^{flox/flox}$ and miR-17-92$^{flox/flox}$;Nkx2-5$^{Cre/+}$ mice was measured. More than 2000 cardiomyocytes were measured from 4 hearts of each genotype.
(n) Reduced cardiac function in cardiac-specific miR-17-92 mutant mice. Echocardiography of cardiac function of 6-month-old miR-17-92$^{flox/flox}$;Nkx2-5$^{Cre/+}$ (cKO) mice and their control littermates. N of each genotype was indicated. *: P<0.05; **: P<0.01. FS: Fractional shortening; LVID;d: Left ventricular end diastolic internal dimension; LVID;s: Left ventricular end systolic internal dimension; LVPW;d: Left ventricular end diastolic posterior wall dimension; LVPW;s: Left ventricular end systolic posterior wall dimension; LV Vol;d: Left ventricular end diastolic volume.

(e) Distribution of isolated adult cardiomyocytes with one (1), two (2) or three (3) and more nuclei from 2 months old hearts of miR-17-92-TG$^{MHC}$ and control mice.

(f) Immunohistochemistry of phosphorylated histone H3 (pH3) on transverse sections of 15 days old control and miR-17-92-TG$^{MHC}$ hearts. Actinin (ACTN1) marks cardiomyocytes and DAPI labels nuclei. Wheat germ agglutinin (WGA) staining marks cell surface (white). White boxes are enlarged in insets.

(g) Quantification of percentages of phosphorylated histone H3 (pH3$^+$) cardiomyocytes of 15 days old control and miR-17-92-TG$^{MHC}$ hearts. N=4 for each genetic group.

(h) Immunohistochemistry of EdU incorporation on transverse sections of 15 days old control and miR-17-92-TG$^{MHC}$ hearts. α-actinin (ACTN1) marks cardiomyocytes and DAPI labels nuclei. Wheat germ agglutinin (WGA) staining marks cell surface (white).

(i) Quantification of percentages of EdU positive cardiomyocytes of 15 days old control and miR-17-92-TG$^{MHC}$ hearts. N=3 for each genetic group.

(j) Cardiac-specific overexpression of miR-17-92 does not change the size of cardiomyocyte. Transverse sections from hearts of 2-month-old miR-17-92$^{TG/TG}$ and miR-17-92$^{TG/TG}$;αMHC-Cre mice were stained with Wheat Germ Agglutinin (WGA) to show the cross section area of cardiomyocyte. Measurement of the cross section area of cardiomyocyte show no significant (ns) difference between two genotypes.

(k) Similar staining and measurement as in 3(j) were also performed on 4-month old heart samples and no significant difference was found between the two genotypes. More than 2000 cardiomyocytes were measured from at least 3 hearts of each genotype. Bar=100 μm.

FIGS. 4a-i. Control of cardiomyocyte proliferation by miR-17-92 in adult heart in response to myocardial infarction (a) Gross morphology of hearts of 6 months old miR-17-92-TG$^{MerCreMer}$ and control mice after tamoxifen administration (upper panels). Haematoxylin and Eosin (H&E) staining of transverse sections of control and miR-17-92-TG$^{MerCreMer}$ hearts (lower panels). Bars=1 mm.

(b) Immunohistochemistry of EdU incorporation on sagittal sections of 6 months old miR-17-92-TG$^{MerCreMer}$ and control mice after tamoxifen administration (upper panels, bar=500 μm); Immunohistochemistry of EdU on sagittal sections of 6 months old miR-17-92-TG$^{MerCreMer}$ and control mice after tamoxifen administration. The arrow points to EdU positive signal in cardiomyocytes. α-actinin (ACTN1) marks cardiomyocytes; DAPI labels nuclei (lower panels, bar=20 μm).

(c) Quantification of total isolated adult cardiomyocytes from hearts of 6 months old miR-17-92-TG$^{MerCreMer}$ and control mice after tamoxifen administration. N=3 for each group.

(d) Quantitative measurement of the size of freshly isolated adult cardiomyocytes from hearts of miR-17-92-TG$^{MerCreMer}$ and control mice. One hundred individual cells from three different hearts were analyzed per group. **P<0.01 between genetic groups.

(e) Scheme of experimental procedure to introduce myocardial infarction (MI), tamoxifin and EdU injection and echocardiography measurement.

(f) Representative images of series of transverse sections of 6 months old miR-17-92-TG$^{MerCreMer}$ and control mice after MI and tamoxifen administration. Sirius red/fast green collagen staining marks myocardium (green) and scar (red). Bars=1 mm.

(g) Quantification of the size of scar in the hearts of miR-17-92-TG$^{MerCreMer}$ (N=4) and control mice (N=5) after MI and tamoxifen administration. *P<0.05 between genetic groups.

(h) Immunohistochemistry of EdU on sagittal sections of 6 months old miR-17-92-TG$^{MerCreMer}$ and control mice after tamoxifen administration. White boxes are enlarged in insets and arrows point to EdU positive signal. α-actinin (ACTN1) marks cardiomyocytes; DAPI labels nuclei. Bars=50 μm).

(i) Induced overexpression of miR-17-92 in the heart. The expression of members of miR-17-92 cluster in 5-month-old heart samples after tamoxifen administration (4 months after tamoxifen administration) in miR-17-92$^{TG/TG}$ and miR-17-92$^{TG/TG}$; αMHC-MerCreMer (MerCreMer) mice was determined by quantitative RT-PCR. N of each genotype was indicated.

FIGS. 5a-i. miR-17-92 regulates cardiomyocyte proliferation and represses the expression and function of PTEN (a) Quantification of percentages of EdU$^+$ cardiomyocytes in cultured neonatal rat cardiomyocytes after treatment with miRNA mimics or control.

(b) Quantification of percentages of EdU$^+$ cardiomyocytes in cultured neonatal rat cardiomyocytes after treatment with miRNA inhibitors or control.

(c) Quantification RT-PCR (qPCR) analyses of CDK1 expression in cultured neonatal rat cardiomyocytes after treatment with miRNA mimics or mimic control.

(d) Quantification of percentages of EdU$^+$ cardiomyocytes in cultured neonatal mouse cardiomyocytes isolated from miR-17-92$^{TG/TG}$ mice and transduced with Ad-cTNT-Cre or Ad-lacZ in control. **P<0.01.

(e) Quantification RT-PCR (qPCR) analyses of the expression of putative miR-17-92 targets the hearts of 20 days old miR-17-92-KO and control mice.

(f) Quantification RT-PCR (qPCR) analyses of the expression of putative miR-17-92 targets the hearts of 15 days old miR-17-92-TG$^{MHC}$ and control mice.

(g) Quantification of percentages of EdU$^+$ cardiomyocytes in cultured neonatal rat cardiomyocytes after treatment with miR-19a/b mimics, control mimics, modify RNA for PTEN (modi-PTEN), or both miR-19a/b mimics and modi-PTEN.

(h) Overexpression of miR-17-92 induces the proliferation of P4 neonatal rat cardiomyocyte. (a) Proliferating neonatal rat cardiomyocytes were determined by detecting the EDU positive cardiomyocyte with immunochemistry. The boxed areas in upper panels are enlarged in lower panels. Bar=60 μm in upper panels; Bar=15 μm in lower panels. (b) Quantification of the percentage of EDU positive cardiomyocyte in each experimental group.

(i) A Western blot showing the overexpression of FLAG-tagged PTEN protein in modified RNA transfected neonatal rat cardiomyocytes.

Figure 5A:
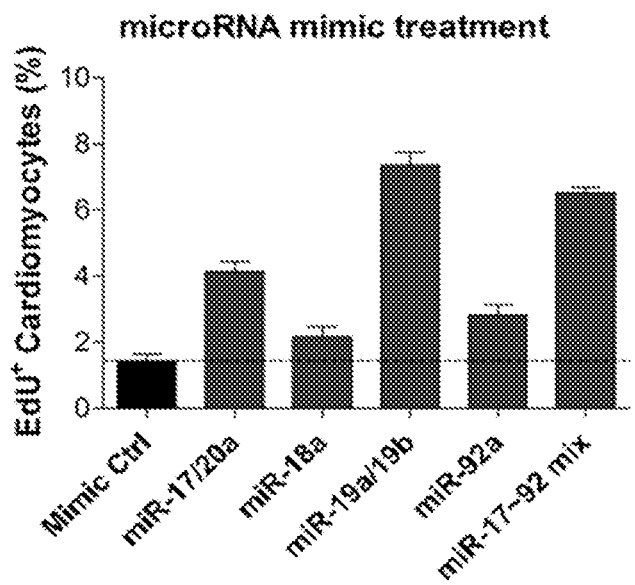
Figure 5B:
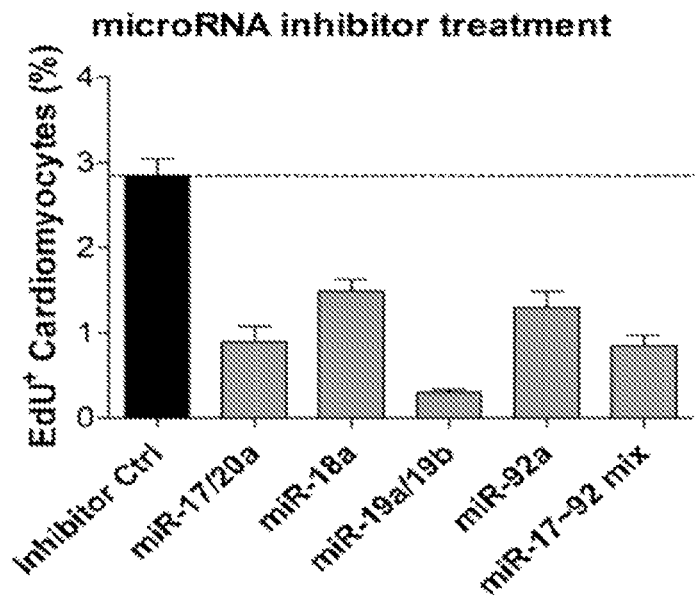
Figure 5C:
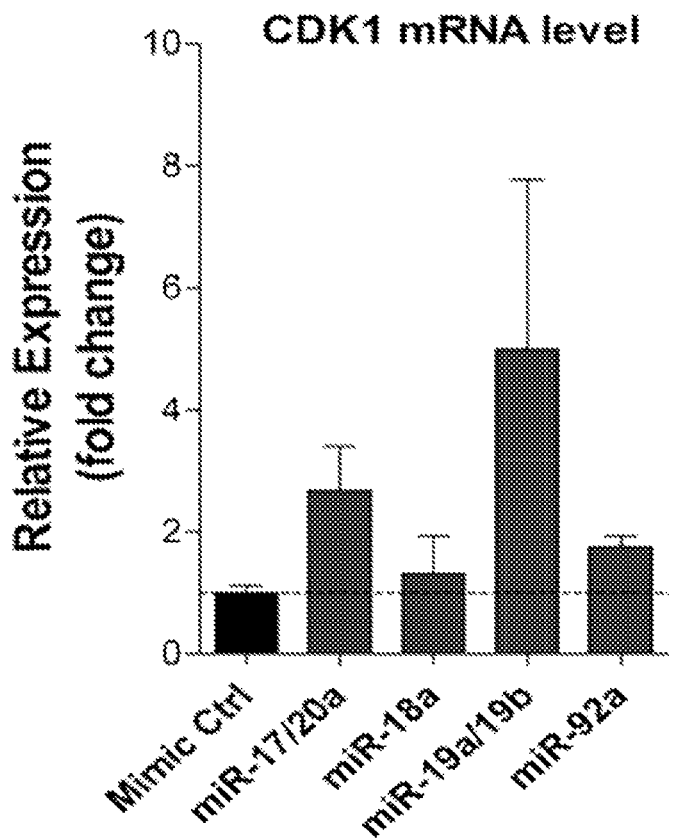
Figure 5D:
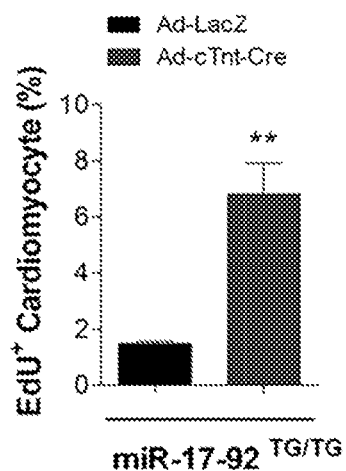
Figure 5E:
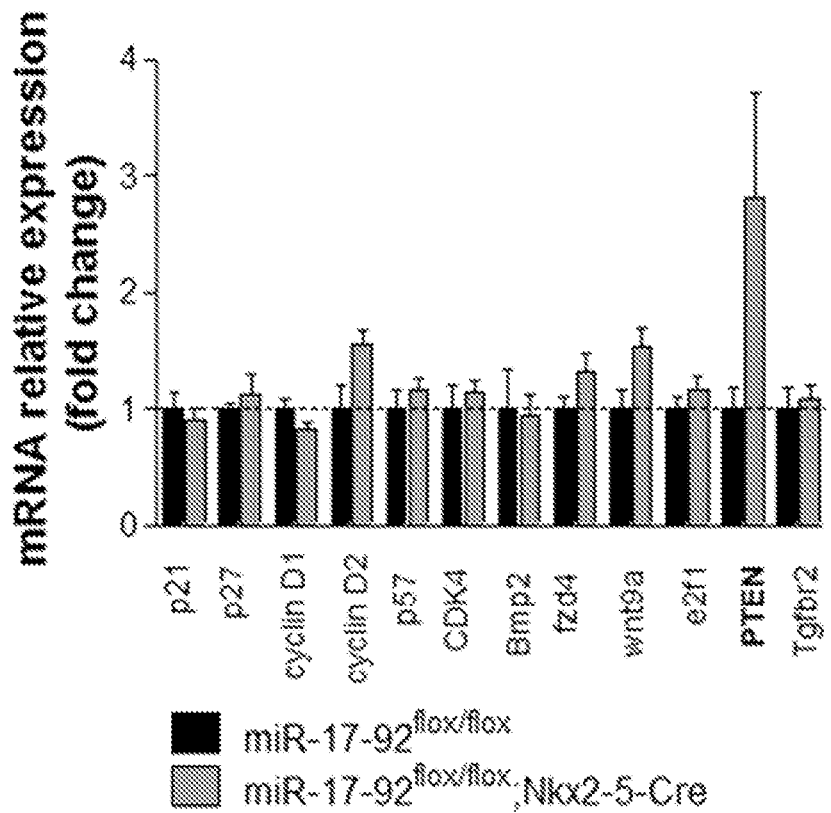
Figure 5F:
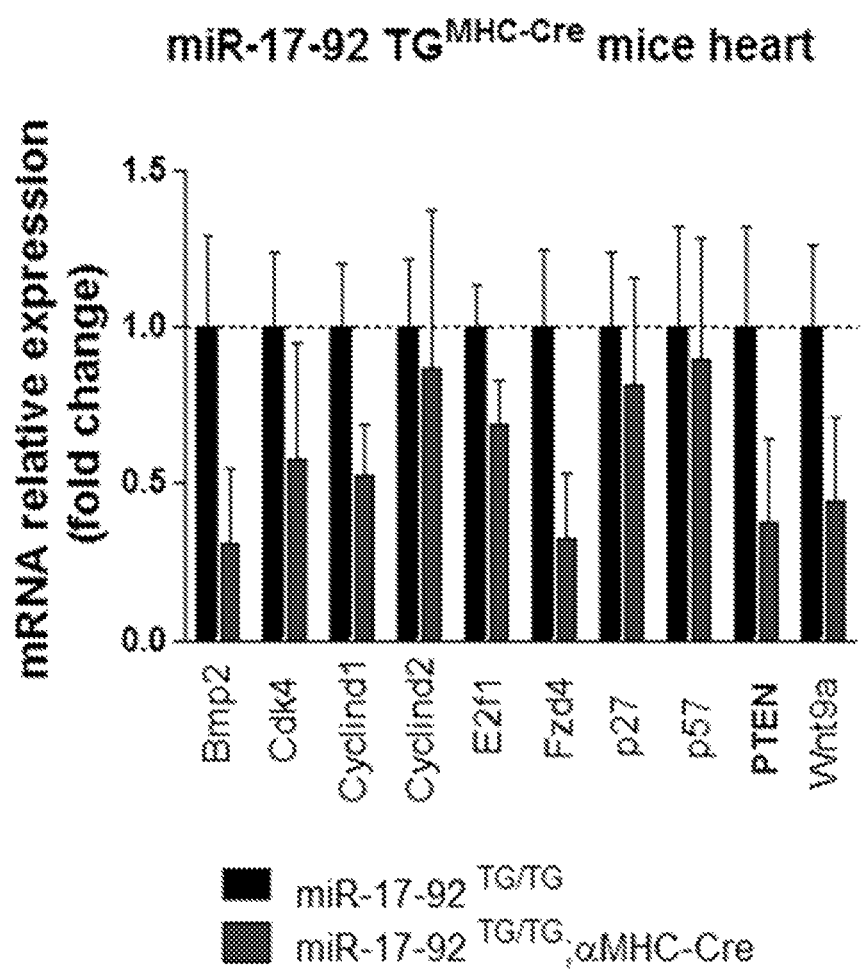
Figure 5G:
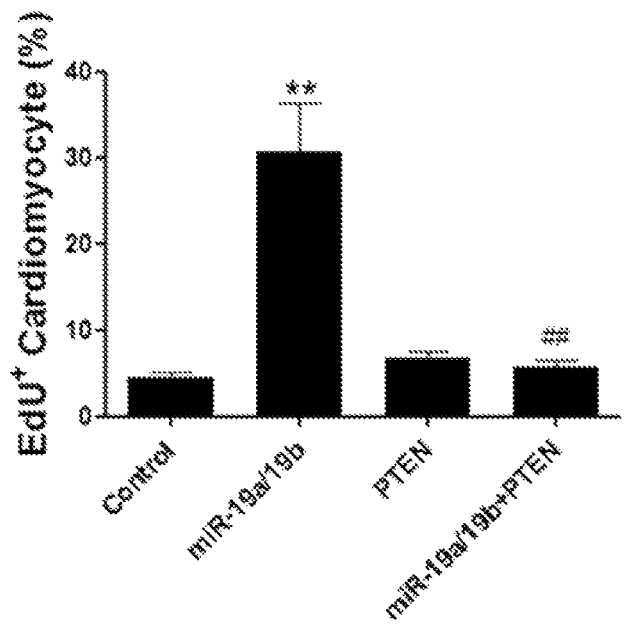
Figure 5H:
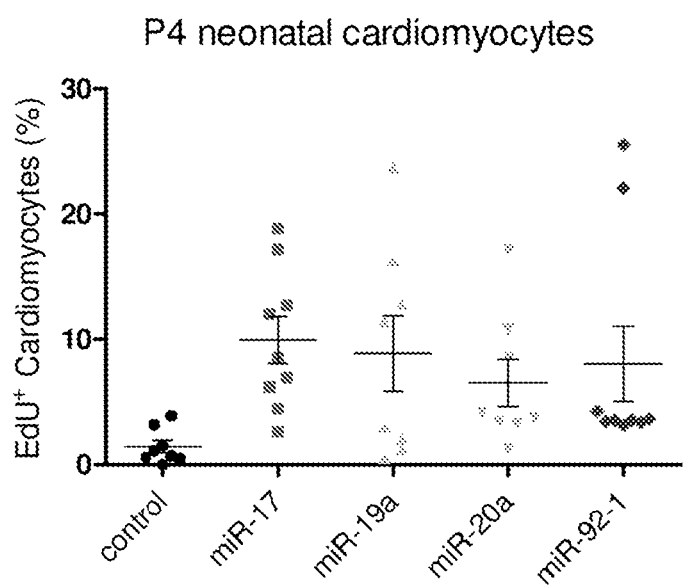
Figures 5I, 6A, 6B, 6C:
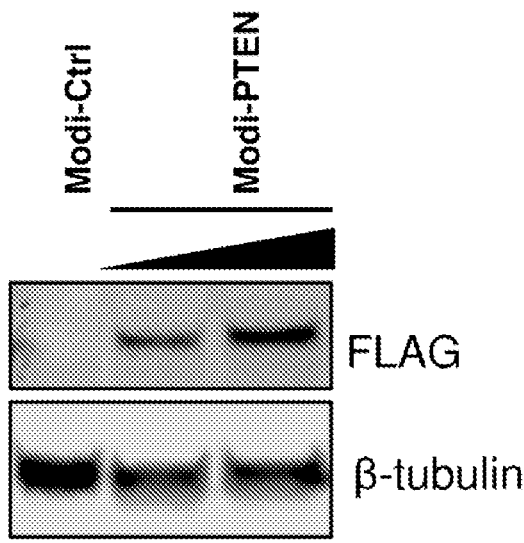

FIGS. 6a-c. Hairpin sequences of miR19a/b (a) Hairpin sequences of human miR19-a.

(b) Hairpin sequences of human miR19-b-1.

(c) Hairpin sequences of human miR19-b-1.

Figure 7A:
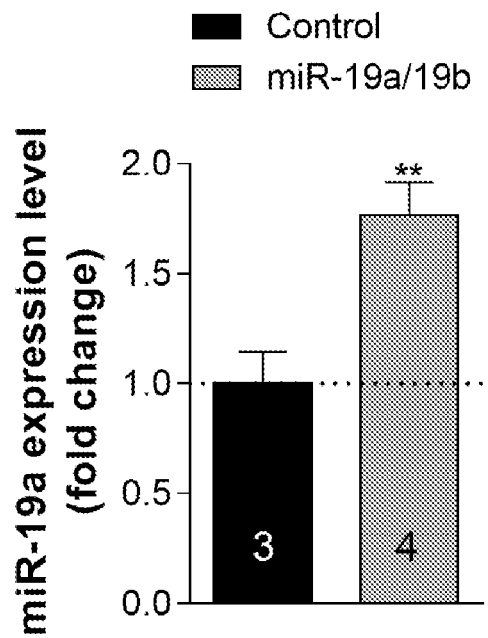

FIG. 7A. Increased expression of miR-19a after intra-cardiac injection of miR-19a/19b mimics in post-myocardial infarction (MI) hearts. Bar graph showing miR-19a expression level determined by real-time Q-PCR using whole heart tissue 3-days after the surgery and mimic injection. N of each group is indicated. **: P<0.01 vs control group.

Figure 7B:
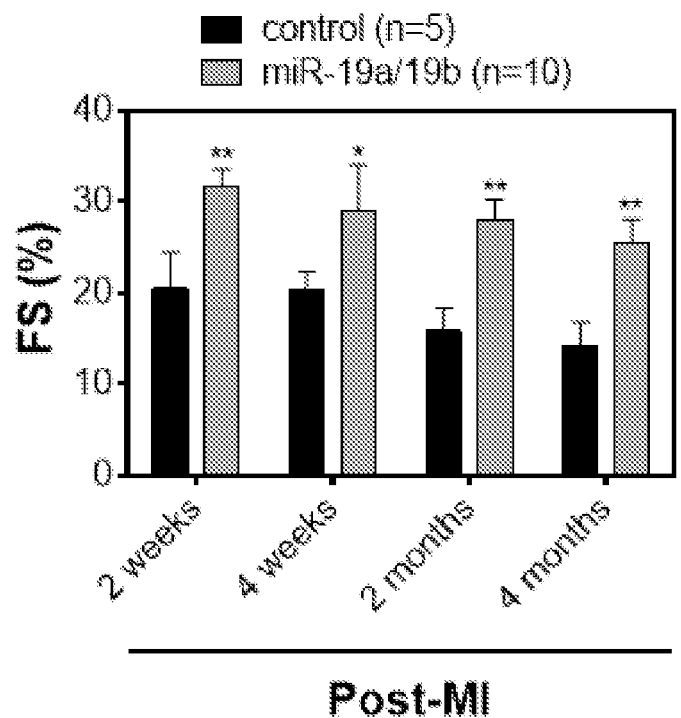

FIG. 7B. Preserved cardiac function after intra-cardiac injection of miR-19a/19b mimics in post-myocardial infarction (MI) hearts. Echocardiography analyses of cardiac function of mice with injection of miR-19a/19b mimics and control post myocardial infarction (MI) 2 weeks to 4 months. FS: Fractional shortening.

Figure 7C:
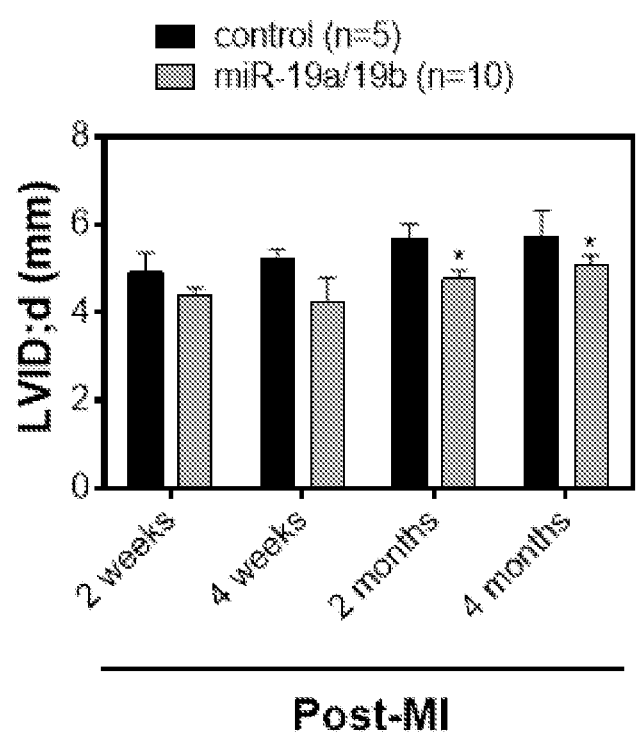

FIG. 7C. Prevent cardiac dilation after intra-cardiac injection of miR-19a/19b mimics in post-myocardial infarction (MI) hearts. Echocardiography analyses of left ventricular internal diastolic dimension (LVID;d) of mice with injection of miR-19a/19b mimics and control post myocardial infarction (MI) 2 weeks to 4 months.

Figure 7D:
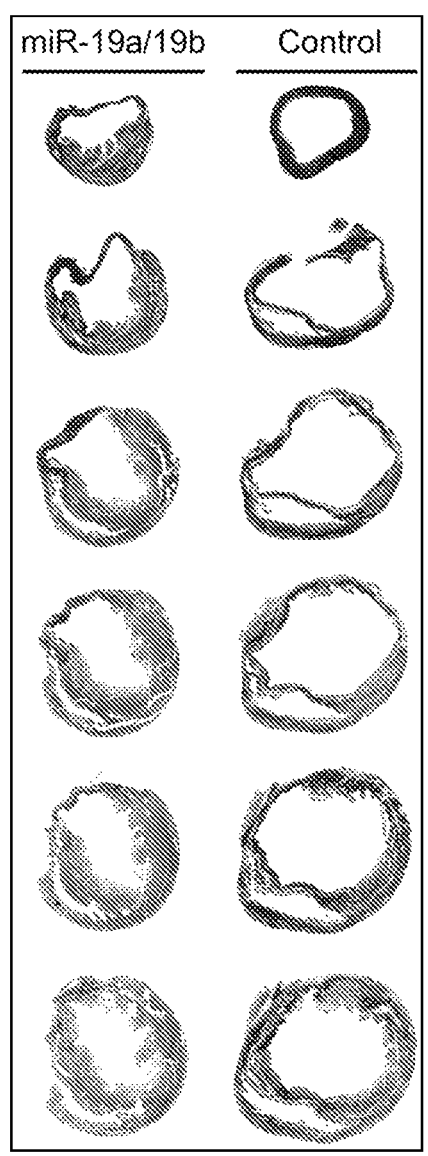

FIG. 7D. Reduced infarct size after intra-cardiac injection of miR-19a/19b miR-19a/19b mimics in post-myocardial infarction (MI) hearts. Representative images of series of transverse sections of hearts 4 weeks after miR-19a/19b or control injection. Sirius red/fast green collagen staining marks myocardium (green) and scar (red).

Figure 7E:
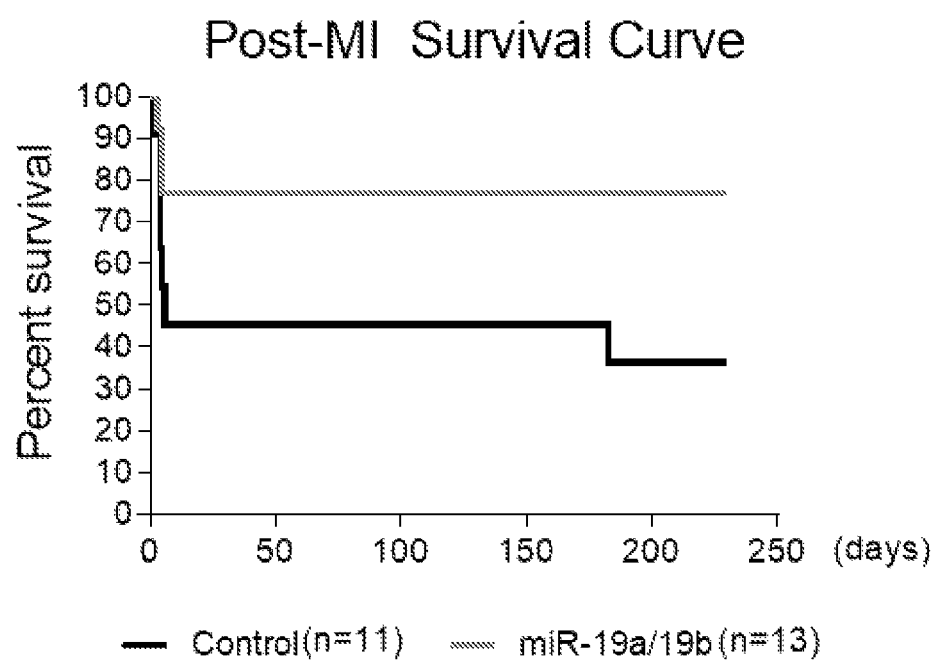

FIG. 7E. Intra-cardiac injection of miR-19a/19b mimics increases survival of post-myocardial infarction (MI) mice.

Figure 8:
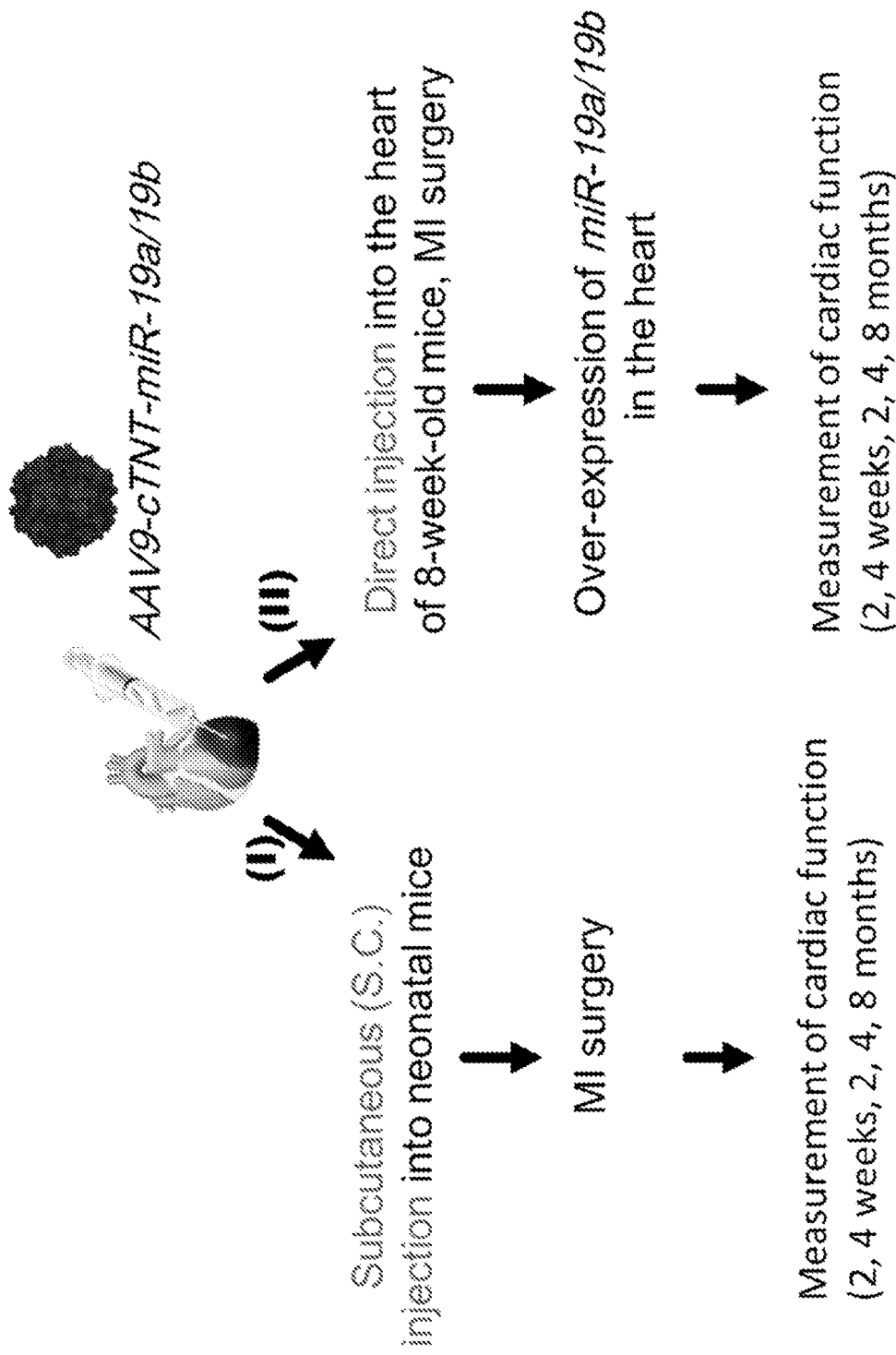

FIG. 8. Schematic diagram of exemplary experiments for cardiac delivery of AAV-miR-19a/19b FIG. 9. S.C. injection of AAV-Luciferase or AAV-eGFP into neonatal mice (P1)

Figure 10:
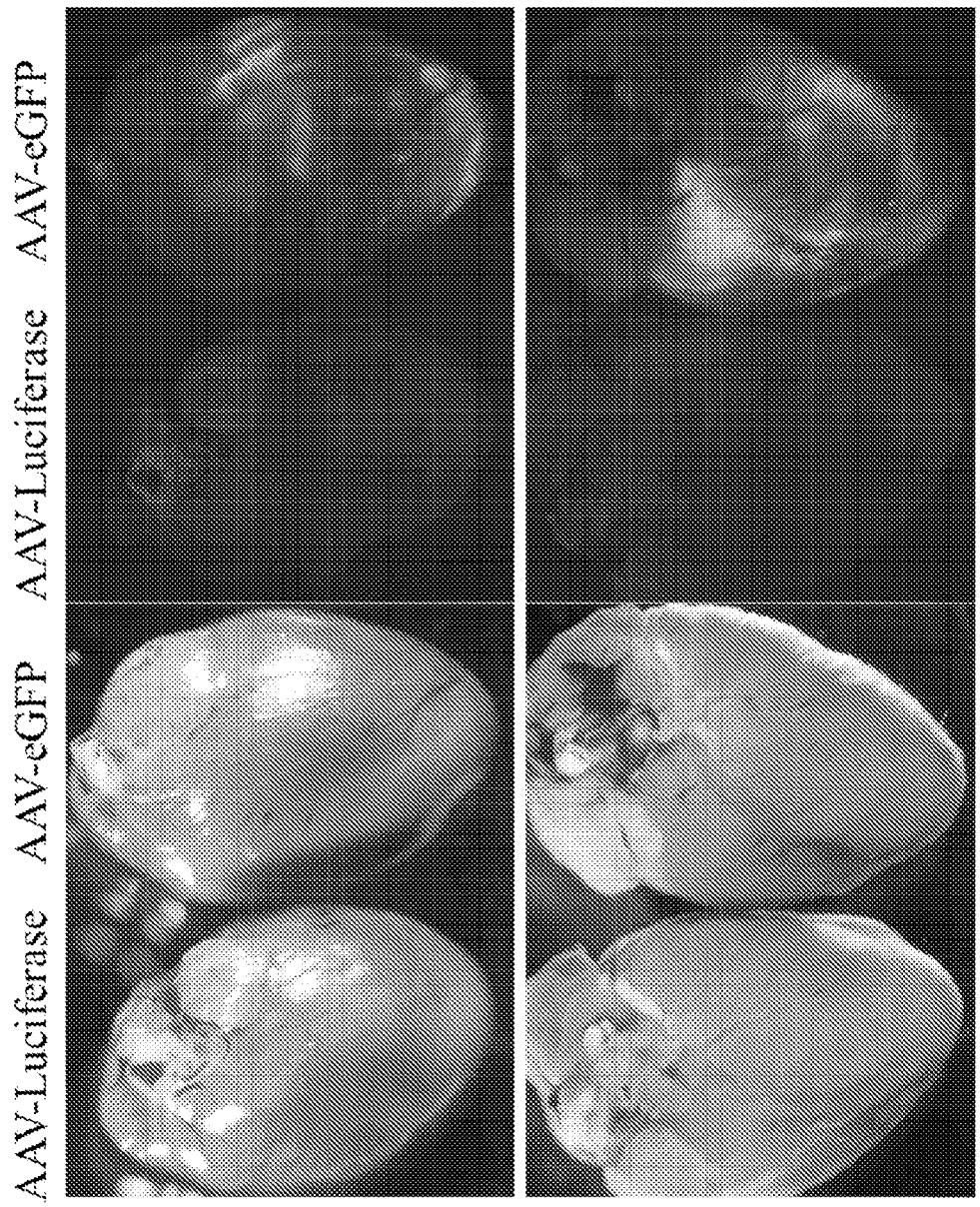

FIG. 10. 2 weeks after direct injection of AAV-Luciferase or AAV-eGFP into adult hearts

DETAILED DESCRIPTION

The adult mammalian heart has limited capability to regenerate itself after the loss of mature cardiomyocytes due to a variety of pathological conditions such as myocardial infarction. It is generally accepted that post-mitotic cardiomyocytes in adult Mammalian hearts exit from the cell cycle and stop cell proliferation[1,2]. However, the hearts of adult zebrafish can undergo cardiac regeneration without scar formation after resection of ventricle, primarily through cardiomyocyte proliferation[3-6]. Intriguingly, a recent report demonstrated that surgical resection of the ventricular apex in newborn mice stimulates the proliferation of cardiomyocytes and repairs the damaged heart, but the mouse heart loses this regenerative potential within 7 days of its postnatal life and it is not clear how the regenerative potential is lost in the adult hearts[7]. To date, the molecular mechanism and regulatory pathways that control adult cardiomyocyte proliferation and cardiac regeneration remain largely unknown.

miRNAs are a class of ~22 nt non-coding RNAs that regulate the expression of protein-coding genes post-transcriptionally. Genes encoding miRNAs are transcribed as long primary transcripts (pri-miRNAs) that contain a stem-loop hairpin structure (Lee et al., EMBO J. 21:4663-70, 2002). Pri-miRNAs are sequentially processed by the RNaseIII enzymes Drosha and Dicer to yield mature miRNA duplexes of 18 to 24 nucleotides in length (Lee et al., Nature 425:415-9, 2003; Hutvagner and Zamore, Science, 297: 2056-60, 2002).

More than 1,000 human miRNAs have been identified; however, the biological functions of many of them remain unknown. The miR-17-92 cluster, a polycistronic miRNA cluster that contains multiple miRNA components (the precursor transcript derived from the mir-17-92 gene contains six tandem stem-loop hairpin structures that yield six mature miRNAs: miR-17, miR-18a, miR-19a, miR-20a, miR-19b-1, and miR-92-1), was initially reported as a human oncogene and named oncomir1[8,9]. Numerous reports have documented the expression of miR-17-92 in variety of human cancers and disorders[10-12]. Genetic studies demonstrated that miR-17-92 is indispensable for mouse development and cell proliferation, and miR-17-92 mutant mice die postnatally, displaying defects in lung, hearts and others[13-15].

The present inventors hypothesized that miR-17-92 might regulate the proliferation of cardiomyocytes. In the present study, the miR-17-92 cluster was tissue-specifically overexpressed or deleted in cardiomyocytes in transgenic or knockout mice. As demonstrated herein, miR-17-92, and specifically miR-19a/b, participates in the regulation of cardiomyocyte proliferation in embryonic, postnatal and adult hearts.

In sharp contrast to embryonic cardiomyocytes, which exhibit strong proliferative activity, the rate of cardiomyocyte proliferation and turn over in adult hearts is very low and it is generally conceived that adult hearts retain very limited (if any) potential for regeneration. As a consequence, the intrinsic renewal rate is insufficient to reverse cardiomyocyte loss and to restore cardiac function under pathophysiological conditions[27,28]. Numerous attempts have been developed to overcome this hurdle and one of the approaches is to induce cell cycle activity in the surviving cardiomyocytes[27,29]. Previous reports indicate that targeted overexpression of members of the cyclin D, cyclin D2 in particularly, is sufficient to induce cardiomyocyte cell cycle activity in adult hearts, resulting in improved cardiac function upon myocardial injury[30-32]. Despite the fact that the critical role of the cell cycle regulators in cardiomyocyte proliferation is known, the molecular pathways that diminish adult cardiomyocyte proliferation remain largely unknown. The studies reported here demonstrated for the first time that miRNAs are previously unidentified regulators of cardiomyocyte proliferation. miR-19a/miR-19b are sufficient and required for neonatal cardiomyocyte proliferation in vitro, consistent with the view that miR-19 is a key component of the miR-17-92 cluster in controlling cell proliferation in postmitotic cardiac myocytes. These miRNAs can be used to reconstitute lost cardiomyocytes in injured adult hearts, and thus are of considerable therapeutic value for human cardiovascular disease.

miRNA 17-92 Cluster miRNAs

MicroRNAs (miRNAs) are a class of small (e.g., 18-24 nucleotides) non-coding RNAs that exist in a variety of organisms, including mammals, and are conserved in evolution. miRNAs are processed from hairpin precursors of about 70 nucleotides which are derived from primary transcripts through sequential cleavage by the RNAse III enzymes drosha and dicer. Many microRNAs can be encoded in intergenic regions, hosted within introns of pre-mRNAs or within ncRNA genes. Many miRNAs also tend to be clustered and transcribed as polycistrons and often have similar spatial temporal expression patterns. MiRNAs have been found to have roles in a variety of biological processes including developmental timing, differentiation, apoptosis, cell proliferation, organ development, and metabolism.

The present methods include the administration and use of miR-17-92 cluster miRNAs, e.g., miR-17, miR-18a, miR-19a, miR-20a, miR-19b-1, and miR-92-1; preferably miRNA 19a and/or 19b, as well as mimics thereof. Preferably human sequences are used, though other sequences are also known in the art and can also be used for the present methods, e.g., in non-human animals. The mouse miRNA sequences are identical to the human sequences.

miRNA-19a

The mature sequence of human miR-19a is UGUG-CAAAUCUAUGCAAAACUGA (SEQ ID NO:1). The mature sequence is excised from the 3' arm of the hairpin precursor. The sequence of the miRNA19a hairpin precursor is GCAGUCCUCUGUUAGUUUUGCAUAGUUGCAC-UACAAGAAGAAUGUAGU UGUGCAAAUCUAUG- CAAAACUGAUGGUGGCCUGC (SEQ ID NO:2), which is coded on chromosome 13. The hairpin structure of miR-19a is shown in FIG. 6a.

miRNA-19b

The mature sequence of human miR-19b-1 is UGUGCAAAUCCAUGCAAAACUGA (SEQ ID NO:3). The mature sequence is excised from the 3' arm of the hairpin precursor. The sequence of the miRNA19b-1 hairpin precursor is CACUGUUCUAUGGUUAGUUUUGCAGGUUUGCAUCCAGCUGUGUGAUAU UCUGCUGUGCAAAUCCAUGCAAAACUGACUGUGGUAGUG (SEQ ID NO:4), which is coded on chromosome 13. The hairpin structure of miR-19b-1 is shown in FIG. 6b.

The mature sequence of human miR-19b-2 is identical to that of miR-19b-1, i.e., UGUGCAAAUCCAUGCAAAACUGA (SEQ ID NO:3). The mature sequence is excised from the 3' arm of the hairpin precursor. The sequence of the miRNA19b-2 hairpin precursor is ACAUUGCUACUUACAAUUAGUUUUGCAGGUUUGCAUUUCAGCGUAUAU AUGUAUAUGUGGCUGUGCAAAUCCAUGCAAAACUGAUUGUGAUAAUGU (SEQ ID NO:5), which is coded on the X chromosome. The hairpin structure of miR-19a is shown in FIG. 6c. Although not part of miR-17-92, miR-19b-2 shares nearly identical (one mismatch) nucleic sequences as miR-19a and likely will functions in the same manner.

miRNA-17

The mature sequence of human miR-17 is CAAAGUGCUUACAGUGCAGGUAG (SEQ ID NO:6). The sequence of the miRNA17 hairpin precursor is GUCAGAAUAAUGUCAAAGUGCUUACAGUGCAGGUAGUGAUAUGUGCAU CUACUGCAGUGAAGGCACUUGUAGCAUUAUGGUGAC (SEQ ID NO:7).

miRNA-18a

The mature sequence of human miR-18a is UAAGGUGCAUCUAGUGCAGAUAG (SEQ ID NO:8). The sequence of the miR-18a hairpin precursor is UGUUCUAAGGUGCAUCUAGUGCAGAUAGUGAAGUAGAUUAGCAUCUAC UGCCCUAAGUGCUCCUUCUGGCA (SEQ ID NO:9).

miRNA-20a

The mature sequence of human miR-20a is UAAAGUGCUUAUAGUGCAGGUAG (SEQ ID NO:10). The sequence of the miR-20a hairpin precursor is GUAGCACUAAAGUGCUUAUAGUGCAGGUAGUGUUUAGUUAUCUACUGC AUUAUGAGCACUUAAAGUACUGC (SEQ ID NO:11).

miRNA-92a

The mature sequence of human miR-92a-1 is UAUUGCACUUGUCCCGGCCUGU (SEQ ID NO:12). The sequence of the miR-92a-1 hairpin precursor, encoded on chromosome 13, is CUUUCUACACAGGUUGGGAUCGGUUGCAAUGCUGUGUUUCUGUAUGGU AUUGCACUUGUCCCGGCCUGUUGAGUUUGG (SEQ ID NO:13).

The mature sequence of human miR-92a-2 is identical to that of miR-92a-1, i.e., UAUUGCACUUGUCCCGGCCUGU (SEQ ID NO:12). The sequence of the miR-92a-2 hairpin precursor is UCAUCCCUGGGUGGGGAUUUGUUGCAUUACUUGUGUUCUAUAUAAAGU AUUGCACUUGUCCCGGCCUGUGGAAGA (SEQ ID NO:14), which is coded on the X chromosome. Although not part of miR-17-92, miR-92a-2 shares nearly identical (one mismatch) nucleic sequences as miR-92a-1 and likely will functions in the same manner.

Seed Sequence

The following table sets forth the seed sequences for the miR-17-92 cluster miRNAS:

| microRNA | Seed sequence | SEQ ID NO: |
| --- | --- | --- |
| miR-17 | AAAGUG | 15 |
| miR-20a | AAAGUG | 16 |
| miR-18a | AAGGUG | 17 |
| miR-19a | GUGCAA | 18 |
| miR-19b | GUGCAA | 19 |
| miR-92a | AUUGCA | 20 |

Methods of Treatment

As described herein, miR-17-92 cluster oligonucleotides can be used to induce proliferation of cardiomyocytes, e.g., in vivo. Thus, these oligonucleotides can be used to treat conditions in which cardiomyocyte proliferation would be desirable, e.g., ischemic injury, e.g., after myocardial infarction (MI); after injury to the heart, e.g., as a result of cardiotoxic drugs (e.g., anthracycline antibiotics (e.g., doxorubicin), cocaine, methamphetamine, cyclic antidepressants, calcium channel blockers, beta-blockers, and digoxin) or trauma (whether accidental or intentional as a result of surgery); heart failure; or diminished cardiac capacity associated with normal aging.

In these methods, a therapeutically effective amount of a miR-17-92 cluster oligonucleotide is administered to the subject. In some embodiments, delivery of the oligonucleotide is targeted to the appropriate cell type, e.g., cardiomyocytes or cardiac tissue, to prevent unwanted side-effects.

A number of methods are known in the art for delivery of miRNA-17-92 cluster oligonucleotides, e.g., using adeno-associated viruses (AAV)- or lentiviral-mediated miRNA delivery (using a method substantially as described in Kota et al., Cell. 137(6): 1005-1017, 2009, or Wang et al., "Increased expression of microRNA-146a decreases myocardial ischaemia/reperfusion injury," Cardiovasc Res. 2013. doi: 10.1093/cvr/cvs356); nano-particle mediated miRNA delivery (e.g., as described in Cheng and Salzman, Mol. Pharmaceutics, 9(5):1481-1488, 2012); gelfoam-mediated intrapericardial miRNA delivery (Polizzotti et al., PLoS One 2012; 7:e36788); and/or direct intramuscular administration of miRNAs in the heart (e.g., as described in Shan et al., "Upregulation of microRNA-1 and microRNA-133 contributes to arsenic-induced cardiac electrical remodeling," Int J Cardiol. 2012. doi:10.1016/j.ijcard.2012.07.009; Kukreja et al., Mol Pharmacol. 80(4): 558-564, 2011).

A preferred way to increase the level of a miRNA is by the use of adenoassociated viruses (AAV), which allows the miRNA to be continually expressed. Additionally, the use of cardiotropic AAV serotypes or mutants improves tissue specificity. Thus, for example, the methods may include delivering the oligonucleotides in a cardiotropic AAV, e.g., as described in Tilemann et al., Circulation Research. 2012; 110: 777-793. In some embodiments, AAV9 is used as described in Bish et al., Human Gene Therapy (2008) 19(12):1359-1368 and Katare et al., Circ Res. 2011 May 13; 108(10):1238-51.

The use of cardiac tissue-specific promoters (e.g., NCX1, TNNT2) for expression allows for further specificity in addition to the AAV serotype. Furthermore, AAV is currently in use in a number of clinical trials for gene therapy, of which the safety profiles have looked quite well. In line with this, Kota et al5 recently showed AAV-mediated delivery of miR-26a blunts tumor genesis in a mouse model of liver cancer.

The methods can include administering oligonucleotides consisting of a mature miRNA sequence (e.g., one, two, or all three of SEQ ID NOs:1, 3, 6, 8, 10 or 12, preferably SEQ ID NOs:1 or 3), or a hairpin sequence (e.g., one, two, or all three of SEQ ID NO:2, 4, 5, 7, 9, 11, 13, or 14, preferably SEQ ID NOs:2 or 4). Alternatively, an oligonucleotide that is shorter than the full length miRNA sequence, but comprises at least the seed sequence of the miRNA, can be administered. The oligonucleotides can thus include at least 7, 8, 9, 10, 11, 12, 13, 14, 15, 16, 17, 18, 19, 20, 21, 22 or 23 of the nucleotides of the mature miRNA, comprising at least the seed sequence, preferably 19 nucleotides or more, and can have up to 20% sequence variation (i.e., non-identity) so long as the oligonucleotides retain the ability to induce proliferation of cardiomyocytes, e.g., as determined be an assay described herein, e.g., an in vitro assay. Preferably any non-identity is outside of the seed sequence, e.g., not in the first 8 nucleotides at the 5' end of the miRNA.

In some embodiments, where sequences longer than the seed sequence are used, the methods include administering both miR-19a and miR-19b oligonucleotides.

In some embodiments, the miR-17-92 cluster oligonucleotides can be administered as synthetic ssRNA, dsRNA, dsDNA, or in an expression vector, e.g., a viral expression vector. In some embodiments, the oligonucleotide is a miRNA mimic, e.g., synthetic RNA duplexes designed to mimic the endogenous functions of the miRNA of interest, with modifications for stability and cellular uptake. The "guide strand" is identical to the miRNA of interest, whereas the "passenger strand" is modified and typically linked to a molecule such as cholesterol for enhanced cellular uptake.

The oligonucleotides can be ssRNA, dsRNA, dsDNA, or miRNA mimics that include one or more modifications, e.g., one or more of the following modifications. The oligonucleotide must function as a miRNA and the cell must recognize it as such, which limits the allowed so the chemical modifications.

In some embodiments, the oligonucleotides comprise at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050. In some embodiments, the oligonucleotides include phosphorothioate at least the first, second, or third internucleotide linkage at the 5' or 3' end of the nucleotide sequence.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. A preferred modification includes 2'-methoxyethoxy[2'-0-CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

Modified nucleobases also comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the oligonucleotides used in the methods described herein comprise one or more locked nucleic acid (LNA) molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. Thus in some embodiments, the oligonucleotides are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-

13253 (1998)). For additional modifications, and discussions of modifications and methods of using the same, see US 20100004320, US 20090298916, and US 20090143326, as well as Egli and Gryaznov, Cellular and Molecular Life Sciences 57(10):1440-1456 (2000); Eulalio et al., "Functional screening identifies miRNAs inducing cardiac regeneration," Nature (2012) doi:10.1038/nature11739; Wang, Methods Mol Biol. 2011; 676:211-23; McManus et al., RNA. 2002 June; 8(6):842-50; and Chorn et al., RNA. 18: 1796-1804 (2012). In some embodiments, the oligonucleotides are 5'-phosphorylated and contain at least one 2'-fluoro ribose modification (Chorn et al., RNA. 18: 1796-1804 (2012)). In some embodiments, the oligonucleotides include a 2'-O-methyl ribosyl substitution at position 2 in the guide strand (Jackson et al., RNA. 2006 July; 12(7): 1197-1205).

The oligonucleotides can be designed using any method known in the art; a number of algorithms are known, and are commercially available (e.g., on the internet, for example at invitrogen.com).

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, the oligonucleotides are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Left., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In general, the oligonucleotides useful in the methods described herein are at least 80% identical to the miRNA, e.g., 90%, 95%, or 100% sequence identity to the miRNA. For example, an oligonucleotide compound in which 18 of 20 nucleobases of the oligonucleotide are identical to a reference miRNA sequence would represent 90 percent identity. Percent identity of an oligonucleotides with a miRNA can be determined routinely using basic local alignment search tools (BLAST programs) (Altschul et al., J. Mol. Biol., 1990, 215, 403-410; Zhang and Madden, Genome Res., 1997, 7, 649-656). Useful oligonucleotides can be identified through routine experimentation. In general the oligonucleotides must retain specificity for their target, i.e., must not directly bind to, or directly significantly affect expression levels of, transcripts other than the intended target.

For further disclosure regarding oligonucleotides, please see US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Making and Using Oligonucleotides

The nucleic acid sequences used to practice the methods described herein, whether RNA, DNA, vectors, viruses or hybrids thereof, can be isolated from a variety of sources, genetically engineered, amplified, and/or expressed or generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

The miR-17-92 oligonucleotides can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising miR-17-92 oligonucleotides.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The oligonucleotides can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

In some embodiments, the oligonucleotides are prepared for administration by mixing with a reagent that enhances delivery, e.g., atelocollagen; INVIVOFECTAMINE, an animal-origin-free lipid based in vivo RNA delivery reagent (Invitrogen); or NLE, which consists of 1,2-dioleoyl-sn-glycero-3-phosphocholine, squalene oil, polysorbate 20, and an antioxidant that forms nanoparticle complexes with synthetic miRNAs in the nanometer diameter range (see, e.g., Trang et al., Mol Ther. 2011 June; 19(6):1116-22).

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration, intraperitoneal (IP) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV or IP administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising oligonucleotides as described herein can be made by lyophilizing a solution comprising a pharmaceutical of the invention and a bulking agent, e.g., mannitol, trehalose, raffinose, and sucrose or mixtures thereof. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

The formulations of the invention can be administered for prophylactic and/or therapeutic treatments. In some embodiments, for therapeutic applications, compositions are administered to a subject who is in need of cardiomyocyte proliferation, e.g., who has had an cardiac injury, e.g., ischemic, e.g., after myocardial infarction (MI); an injury to the heart, e.g., as a result of cardiotoxic drugs (e.g., anthracycline antibiotics (e.g., doxorubicin), cocaine, methamphetamine, cyclic antidepressants, calcium channel blockers, beta-blockers, and digoxin) or trauma (whether accidental or intentional as a result of surgery); heart failure; or diminished cardiac capacity associated with normal aging; or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to improve cardiac function, increase cardiac contractile force, or increase the thickness of the myocardium in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of cardiomyocyte proliferation generated after each administration, i.e., as measured by improved cardiac function, increased cardiac contractile force, or increased thickness of the myocardium, and the like. The formulations should provide a sufficient quantity of active agent to effectively treat, prevent or ameliorate conditions, diseases or symptoms as described herein.

Various studies have reported successful mammalian dosing using nucleic acid sequences. For example, Esau C., et al., (2006) Cell Metabolism, 3(2):87-98 reported dosing of normal mice with intraperitoneal doses of miR-122 anti-sense oligonucleotide ranging from 12.5 to 75 mg/kg twice weekly for 4 weeks. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg $kg^{-1}$ LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the oligonucleotides can be co-administered with cardiac progenitor or stem cells (e.g., as described in Boyle et al., Circulation. 2006; 114: 339-352, or with oligonucleotides comprising hsa-miR-590 and/or hsa-miR-199a (e.g., as described in Eulalio et al., 2012, supra), for treating or reducing risk of a disorder described herein.

EXAMPLES

The invention is further described in the following examples, which do not limit the scope of the invention described in the claims.

Materials and Methods

The following materials and methods were used in examples 1-5 described herein.

Animals

All experiments with mice were performed according to protocols approved by the Institutional Animal Care and Use Committees of Boston Children's Hospital. miR-17-92$^{flox/flox}$ (Ventura A, et al. (2008) Targeted deletion reveals essential and overlapping functions of the miR-17 through 92 family of miRNA clusters. Cell 132:875-886), miR-17-92$^{TG/TG}$ (Xiao C, et al. (2008) Lymphoproliferative disease and autoimmunity in mice with increased miR-17-92 expression in lymphocytes. Nat Immunol 9:405-414), Nkx2-5$^{Cre/+}$ (Moses K A, DeMayo F, Braun R M, Reecy J L, Schwartz R J (2001) Embryonic expression of an Nkx2-5/Cre gene using ROSA26 reporter mice. Genesis 31:176-180), αMHC-Cre (Oka T, et al. (2006) Cardiac-specific deletion of Gata4 reveals its requirement for hypertrophy, compensation, and myocyte viability. Circ Res 98:837-845), αMHC-MerCreMer (Sohal D S, et al. (2001) Temporally regulated and tissue-specific gene manipulations in the adult and embryonic heart using a tamoxifen-inducible Cre protein. Circ Res 89:20-25) were described previously.

Cardiac-Specific Knockout of miR-17-92 Cluster in Mice

The miR-17-92$^{flox/+}$ mice harbor an allele of loxP-flanked miR-17-92 cluster. miR-17-92$^{flox/flox}$ mice were crossed with Nkx2-5$^{Cre/+}$ mice, in which the expression of Cre recombinase is controlled by the endogenous promoter of cardiac-specific marker gene, Nkx2-5, to generate the miR-17-92$^{F/+}$;

Nkx2-5$^{Cre/+}$ offsprings. The miR-17-92$^{flox/+}$;Nkx2-5$^{Cre/+}$ mice were then crossed back to miR-17-92$^{flox/flox}$ mice to obtain the miR-17-92 conditional (cardiac-specific) knockout (cKO) mice (miR-17-92$^{flox/flox}$;Nkx2-5$^{Cre/+}$).

Cardiac-Specific Overexpression of miR-17-92 Cluster in Mice miR-17-92$^{TG/+}$ mice harbor the miR-17-92 transgene targeted to the Gt(ROSA)26Sor locus. The miR-17-92 transgene has a loxP-flanked Neo-STOP cassette preventing transcription of the downstream human miR-17-92 cluster. When bred to mice that express Cre recombinase, the resulting offspring will have the STOP cassette deleted in the Cre-expressing tissue resulting in ectopic expression of the miR-17-92 cluster. miR-17-92$^{TG/+}$ mice were crossed with Nkx2-5$^{Cre/+}$ mice and αMHC-Cre mice, respectively, to obtain the miR-17-92$^{TG/+}$;Nkx2-5$^{Cre/+}$ offsprings and miR-17-92$^{TG/+}$;αMHC-Cre offsprings. miR-17-92 cluster is cardiac-specific overexpressed in these offsprings. miR-17-92$^{TG/+}$ mice were crossed with αMHC-MerCreMer (MerCreMer) to obtain miR-17-92$^{TG/+}$;MerCreMer offsprings for inducible cardiac-specific overexpression of miR-17-92 cluster. In order to achieve the induction of overexpression, tamoxifen was administrated in these mice. EdU was administered intraperitoneally at 5 μg per g of body weight (adult), 6 times for continuous day.

Ischemic Injury Model-Myocardial Infarction (MI)

Myocardial infarction (MI) was induced by ligation of left anterior descending coronary artery. 8 week old male C57 mice were randomly selected to undergo coronary artery ligation or sham surgery. For surgery, mice were anesthetized with isoflurane (3% isoflurane for induction, 2% isoflurane for maintenance). The chest was shaved and cleaned with alcohol. A suture was placed around the front upper incisors and pulled taut so that the neck was slightly extended. The tongue was retracted and held with forceps, and a 20-G catheter was inserted into the trachea. The catheter was then attached to the mouse ventilator via a Y-shaped connector. Ventilation was performed with a tidal volume of 225 μl for a 25 g mouse and a respiratory rate of 130 breaths/min. 100% oxygen was provided to the inflow of the ventilator. The chest was opened through a left parasternal incision, and the heart exposed at the left 3rd-4th intercostal space. Chest retractor was applied to facilitate the view. The pericardium was opened, and ligations made on the left anterior descending coronary artery (LAD) using 8-0 silk sutures (Ethicon). The lungs were slightly overinflated to assist in removal of air in the pleural cavity.

All mice were given a single dose of 10 μg synthetic microRNA-19a/b (Dharmacon, Lafayette, Colo.) (miR-19a: UGUGCAAAUCUAUGCAAAACUGA (SEQ ID NO:1; miR-19b: UGUGCAAAUCCAUGCAAAACUGA; SEQ ID NO:3) formulated with NLE according to the manufacturer's instructions by intra-myocardium injection. The NLE (MaxSuppressor in vivo RNALancerII) was purchased from BIOO Scientific, (Austin, Tex.). NLE consists of 1,2-dioleoyl-sn-glycero-3-phosphocholine, squalene oil, polysorbate 20, and an antioxidant that forms nanoparticle complexes with synthetic miRNAs in the nanometer diameter range.

Sham operations were performed similarly, but without ligation of the artery. The chest cavity was closed with 6-0 silk sutures (Ethicon), the skin incision was closed by liquid topical adhesive (Nexaband), anesthesia was discontinued, and the animal was observed until conscious. The duration of each procedure was about 15-20 mins Postoperative analgesics (0.05-0.1 mg/kg Buprenorphine s.c.) ware given every 8-12 h for 48 hours. About 6-15 mice ware used for each experimental group.

Measurement of Cardiac Function by Echocardiography

Echocardiographic measurements were performed on mice using a Visual Sonics Vevo® 2100 Imaging System (Visual Sonics, Toronto, Canada) with a 40 MHz MicroScan transducer (model MS-550D). Mice were anesthetized with isoflurane (2.5% isoflurane for induction and 0.5% for maintenance). Heart rate and left ventricular (LV) dimensions, including diastolic and systolic wall thicknesses, LV end-diastolic and end-systolic chamber dimensions were measured from 2-D short-axis under M-mode tracings at the level of the papillary muscle. LV mass and functional parameters such as percentage of fractional shortening (FS %) and left ventricular volume were calculated using the above primary measurements and accompanying software.

Modified RNA (ModRNA)

The modified RNA (ModRNA) experiment was performed essentially as described (Warren L, et al. (2010) Highly efficient reprogramming to pluripotency and directed differentiation of human cells with synthetic modified mRNA. Cell Stem Cell 7:618-630). Briefly, the "universal" ModRNA backbone was generated by modifying previously described pcDNA3.3-TOPO-cMyc ORF plasmid containing T7 promoter and optimized 5' and 3' untranslated regions (pcDNA3.3-TOPO-T7-5'UTR-cMyc-3'UTR). The pcDNA3.3-TOPO backbone with 5'/3'UTRs (pcDNA3.3-TOPO-5'3'UTRs) was amplified by long-range PCR (PrimeStar high fidelity DNA polymerase, Takara). Two unique restriction sites for AscI and NheI were incorporated into the PCR products, in order to create the 5' and 3' sticky ends. The ORF of PTEN cDNA was PCR amplified and first cloned into the pcDNA3-N-Flag vector. The fusion Flag-PTEN ORF was then amplified using forward primer containing NheI site and reverse primer with AscI site, and sub-cloned into the pcDNA3.3-TOPO-5' and 3'UTRs backbone to generate the pcDNA3.3-TOPO-T7-5'UTR-Flag-PTEN-3'UTR.

Cardiomyocyte Isolation and Culture

Neonatal rat and mouse cardiomyocytes were prepared as previously described (Tatsuguchi M, et al. (2007) Expression of microRNAs is dynamically regulated during cardiomyocyte hypertrophy. J Mol Cell Cardiol 42:1137-1141). Briefly, Neonatal rat and mouse cardiomyocytes were isolated by enzymatic disassociation of one day-old or four day-old (P1 or P4) neonate hearts with the Neonatal Cardiomyocyte Isolation Kit (Cellutron, Baltimore Md.). Cardiomyocytes were plated differentially for 2 hours to remove fibroblasts. Cells were plated on 1% gelatin coated plates in medium containing 10% horse serum and 5% fetal calf serum (FCS). After 24 hours of plating, cells were changed into serum-free medium overnight. Then, 100 nM of microRNA mimic duplex or 200 nM microRNA hairpin inhibitors of miR-17-92 cluster members and negative control oligonucleotide (Dharmacon) were transfected into cardiomyocyte by using Lipofectamine RNAiMAX (Invitrogen) transfection reagent. After 6 hours transfection, the cultures were changed to serum free medium for mimic experiments and changed to 1% FCS medium for inhibitor experiments. EdU (5-ethynyl-2'-deoxyuridine, Invitrogen) was added, 24 hours later, cells were fixed and harvested for Q-PCR analyses and immunohistochemistry analyses.

Adult mouse cardiomyocyte were isolated using a previously described procedure (O'Connell T D, et al. (2006) Alpha1-adrenergic receptors prevent a maladaptive cardiac response to pressure overload. J Clin Invest 116:1005-1015)

with minor modifications. Briefly, following perfusion and digestion of the heart with collagenase II (Worthington Biochemical Corp, Lakewood, N.J.), dissociated cells (myocytes and non-myocytes) were sedimented by gravity. The bottom layer is rich in adult cardiomyocyte for cell counting and staining.

Quantitative RT-PCR

Total RNAs were isolated using Trizol Reagent (Invitrogen) from cell or tissue samples. For quantitative RT-PCR detecting the expression of protein-coding gene, 2.0 µg RNA samples were reverse-transcribed to cDNA using random hexamers and MMLV reverse transcriptase (Invitrogen) in 20 µl reaction system. In each analysis, 0.1 µl cDNA pool was used for quantitative PCR. For quantitative RT-PCR detecting the expression of miRNAs, 10 ng RNA samples were reverse-transcribed to cDNA by using TaqMan® MicroRNA Reverse Transcription Kit (ABI). In each analysis, 1.5 µl cDNA pool and TaqMan® MicroRNA Assays were used for quantitative PCR. For target gene expression, Real time PCR was performed with SYBR Green detection. All qPCR experiments were performed on the Applied Biosystems 7500 Real-Time PCR System.

Histology and Immunostaining

Mouse hearts were dissected out, rinsed with PBS and fixed in 4% paraformaldehyde (pH 8.0) overnight. After dehydration through a series of ethanol baths, samples were embedded in paraffin wax according to standard laboratory procedures. Sections of 5 µm were stained with Haematoxylin and Eosin (H&E) for routine histological examination with light microscope.

To determine infarct size, hearts were fixed in 4% PFA, dehydrated and embedded in paraffin. Then the embedded paraffin blocks were cut through from apex to base. The first 10 sections (10 µm thickness each) of every 100 sections were used. Sections were stained with Sirius Red-Fast Green. Infarct size was calculated according to the formula:

[length of coronal infarct perimeter(epicardial+endocardial)/total left ventricle coronal perimeter (epicardial+endocardial)]×100

(Pfeffer J M, Pfeffer M A, Fletcher P J, Braunwald E (1991) Progressive ventricular remodeling in rat with myocardial infarction. Am J Physiol 260:H1406-1414).

Immunofluorescence was performed on paraformaldehyde (PFA)-fixed, paraffin-embedded heart sections. After deparaffinization, re-hydration and heat-induced epitope retrieval, sections were incubated with antibodies, rabbit phospho-Histone H3 (pH3, 1:400, Millipore, cat #06-570), anti-mouse α-actinin (ACTN1, 1:250, Abcam, cat# ab9465) and goat anti-rabbit AlexaFluor 488 and goat anti-mouse AlexaFluor 594 secondary antibody (1:400, Invitrogen). Images were captured using confocal microscopy (FV1000, Olympus). Quantitative data were obtained by measuring co-localization of 4',6-diamidino-2-phenylindole DAPI (nuclear staining) with pH3 in the cardiomyocyte area. EdU was detected with Click-iT chemistry (Invitrogen). Imaging was performed on a Nikon TE2000 epifluorescent microscope with deconvolution (Volocity; PerkinElmer) or on an Olympus FV1000 confocal.

Statistics

Values are reported as means±SEM unless indicated otherwise. The 2-tailed Mann-Whitney U test was used for comparing 2 means (Prism, GraphPad). Values of P<0.05 were considered statistically significant.

Figure 1B:
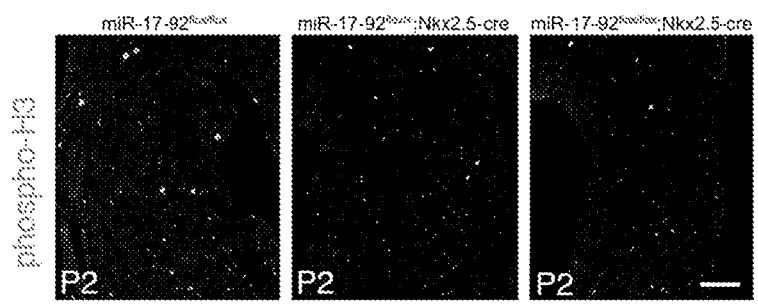
Figure 1C:
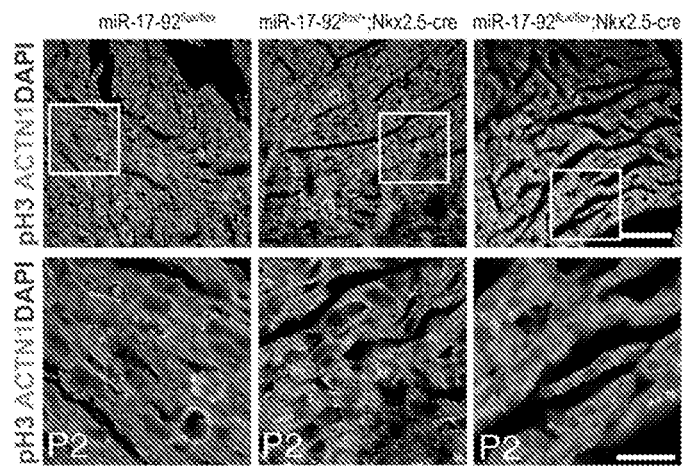
Figure 1D:
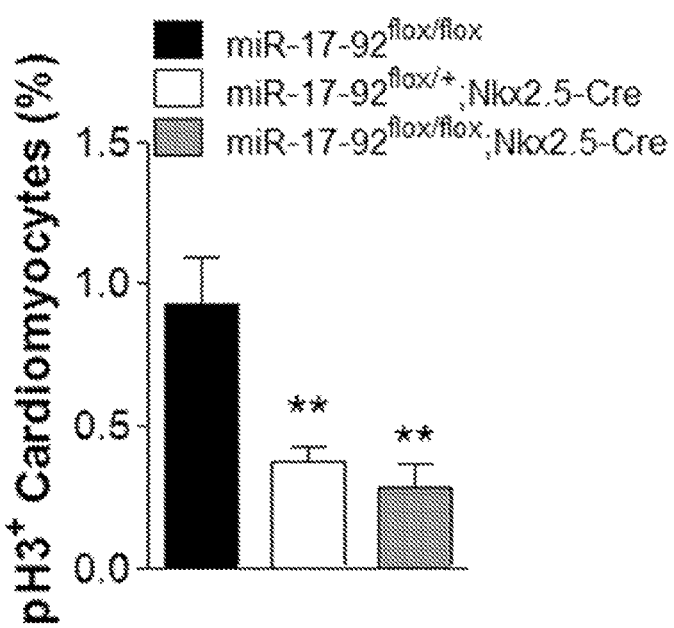
Figure 1E:
Figure 1F:
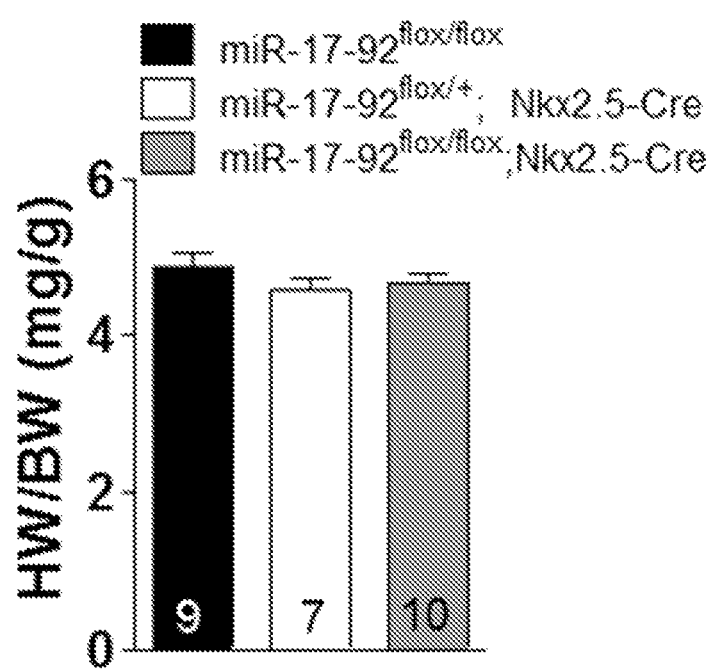
Figure 1G:
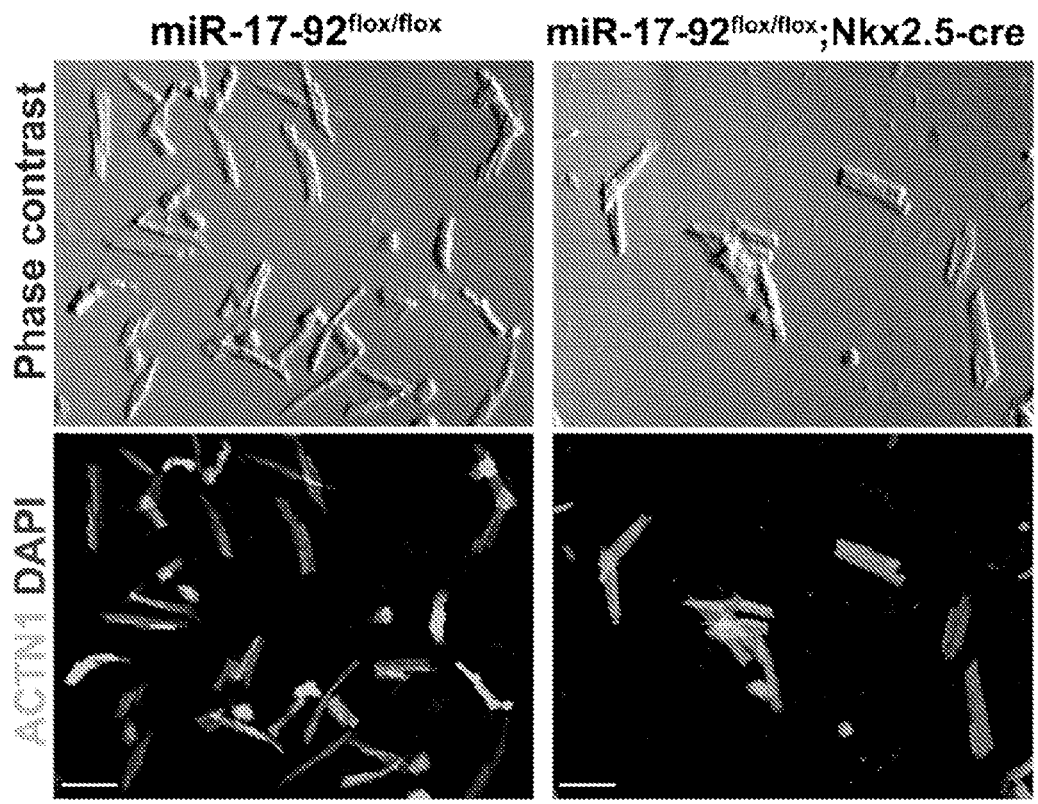
Figure 1H:
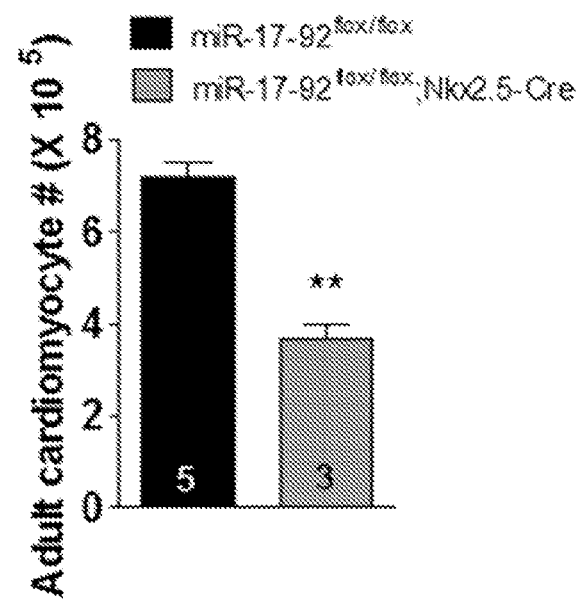
Figures 1I, 1J, 1K:
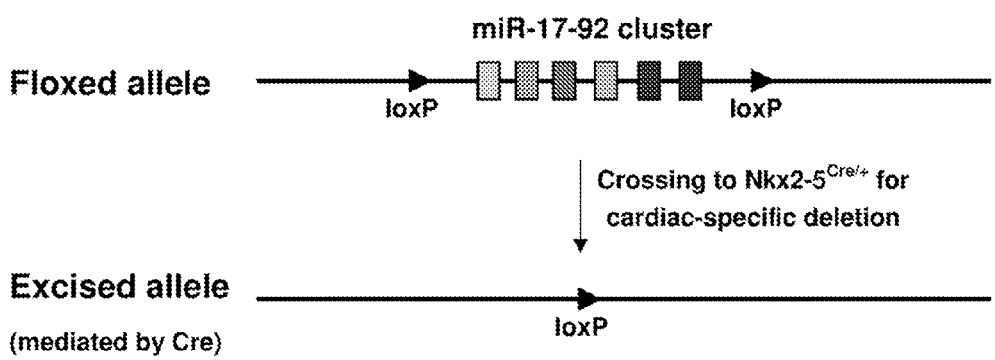
Figure 1L:
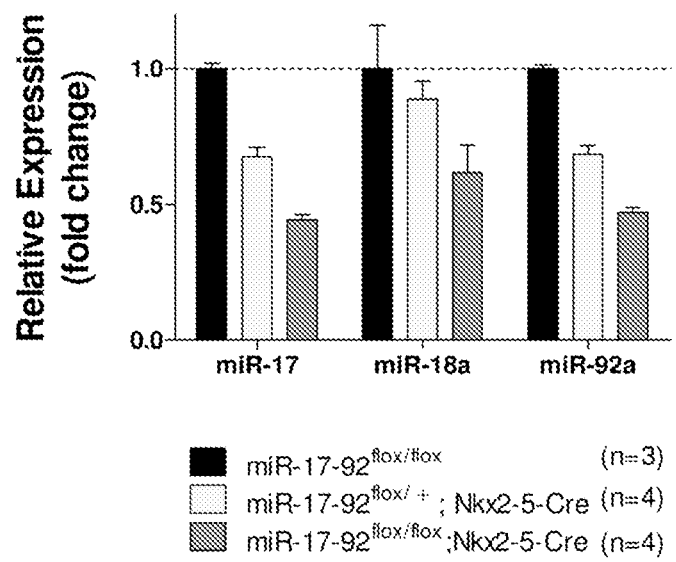

Example 1 miR-17-92 is Required for Cardiomyocyte Proliferation in Embryonic and Postnatal Hearts miR-17-92$^{flox/flox}$ mice[15] were crossed with Nkx2.5-Cre mice, in which the expression of Cre recombinase was under the control of the cardiac-specific Nkx2.5 gene, to delete miR-17-92 in embryonic, postnatal and adult hearts (FIG. 1j). Cardiac-specific miR-17-92 mutant mice (named miR-17-92-cKO) ware slightly under-representative at weaning age (20.3%), suggesting that cardiac-specific deletion of miR-17-92 resulted in partial embryonic lethality (FIG. 1k). The expression of miR-17-92 miRNAs was significantly reduced in the hearts of mutant mice (FIG. 1l).

The hearts of postnatal miR-17-92-cKO mice were substantially smaller than that of their littermate controls (FIG. 1a). The proliferation of cardiomyocytes was examined in miR-17-92-cKO hearts, using immunostaining for phosphorylated histone H3 (pH3) which marks mitosis. There was less proliferating cardiomyocytes in postnatal hearts of miR-17-92-cKO mice (FIG. 1b, c). Quantitative analyses confirmed substantial decrease in total numbers of pH3 positive cardiomyocytes in miR-17-92-cKO hearts (FIG. 1d). A decrease in cardiomyocyte proliferation was also observed in miR-17-92 heterozygous hearts (FIG. 1d).

Figure 1M:
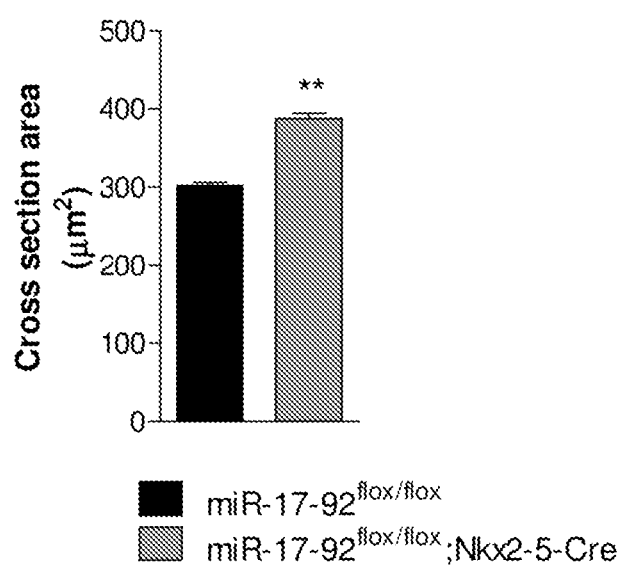
Figure 1N:
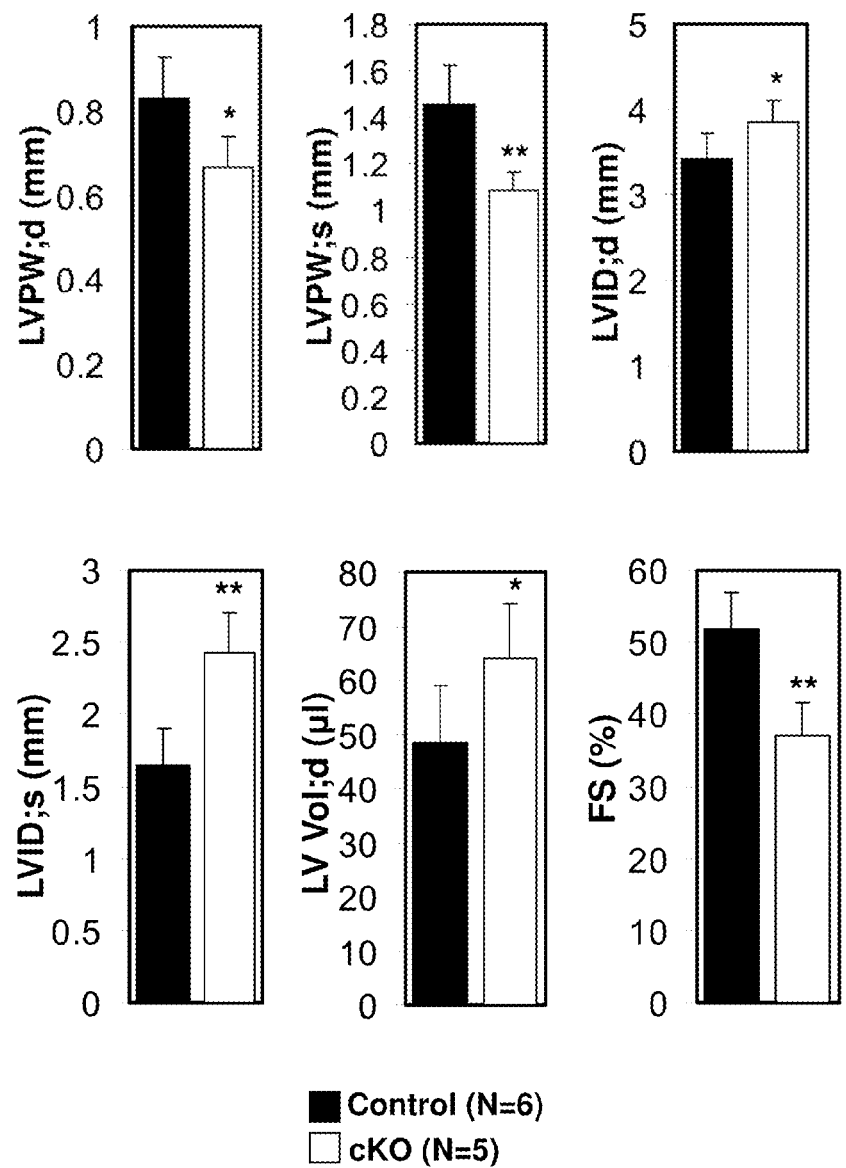

Most miR-17-92-cKO mice survived to adulthood, so miR-17-92 loss-of-function phenotype in adult hearts was investigated. The miR-17-92-cKO hearts were smaller than that of their littermate controls (FIG. 1e). The heart weight (HW) to body weight (BW) ratio was not altered in miR-17-92-cKO mice (FIG. 1f). This is likely due a compensatory cardiomyocyte hypertrophy in these hearts (FIG. 1m). The Langendorf perfusion method was used to isolate and quantify total cardiomyocyte numbers from adult hearts; a substantial decrease in the total numbers of cardiomyocytes was found in the hearts of miR-17-92-cKO mice (FIG. 1g, h). Quantitative measurement of the size of isolated adult cardiomyocytes showed that the size of cardiomyocytes was increased in the heart of miR-17-92-cKO mice (FIG. 1i), consistent with the idea that increased size of cardiomyocytes compensates for the reduction of total numbers of cardiomyocytes in mutant hearts. Cardiac function was examined using echocardiography, and decreased ventricle wall thickness, increased ventricle systolic diameter and decreased cardiac function were found in miR-17-92-cKO mice when compared with their littermate controls (Table 1 and FIG. 1n). Together, these results indicate that miR-17-92 is required for cardiomyocyte proliferation and normal cardiac function in postnatal and adult hearts.

TABLE 1

Table 1. Echocardiography analyses of cardiac function of different aged cardiac-specific miR-17-92 knockout mice (cKO, miR-17-92flox/flox; Nkx2-5Cre/+) and their control littermates.

|  | 2-month-old | | 6-month-old | | 13-month-old | |
|---|---|---|---|---|---|---|
|  | Control (N = 6) | cKO (N = 6) | Control (N = 6) | cKO (N = 5) | Control (N = 6) | cKO (N = 6) |
| IVS; d (mm) | 0.663 ± 0.051 | 0.616 ± 0.066 | 0.796 ± 0.117 | 0.633 ± 0.101* | 0.805 ± 0.092 | 0.693 ± 0.067* |
| IVS; s (mm) | 1.159 ± 0.172 | 1.068 ± 0.110 | 1.172 ± 0.063 | 0.794 ± 0.072** | 1.142 ± 0.103 | 0.853 ± 0.066** |
| LVID; d (mm) | 3.361 ± 0.455 | 3.358 ± 0.285 | 3.416 ± 0.305 | 3.842 ± 0.260* | 3.604 ± 0.167 | 3.555 ± 0.224 |
| LVID; s (mm) | 1.606 ± 0.263 | 1.928 ± 0.325 | 1.646 ± 0.251 | 2.420 ± 0.287** | 1.715 ± 0.200 | 2.259 ± 0.289** |
| LVPW; d (mm) | 0.693 ± 0.073 | 0.756 ± 0.172 | 0.827 ± 0.098 | 0.665 ± 0.074* | 0.789 ± 0.097 | 0.749 ± 0.058 |
| LVPW; s (mm) | 1.291 ± 0.097 | 1.251 ± 0.154 | 1.453 ± 0.171 | 1.089 ± 0.072** | 1.425 ± 0.221 | 1.115 ± 0.101* |
| EF (%) | 84.33 ± 2.36 | 74.62 ± 7.29* | 83.69 ± 4.26 | 67.54 ± 6.05** | 84.15 ± 3.42 | 67.25 ± 5.83** |
| FS (%) | 52.32 ± 2.58 | 42.82 ± 6.17** | 51.88 ± 5.09 | 37.12 ± 4.58** | 52.48 ± 4.04 | 36.69 ± 4.66** |
| LV Mass (mg) | 72.14 ± 19.24 | 72.54 ± 20.07 | 94.22 ± 24.60 | 83.27 ± 10.80 | 99.21 ± 17.76 | 84.88 ± 14.39 |
| LV Mass (Corrected, mg) | 57.71 ± 15.39 | 58.03 ± 16.05 | 75.37 ± 19.68 | 66.62 ± 8.64 | 79.36 ± 14.20 | 67.90 ± 11.52 |
| LV Vol; d (uL) | 47.25 ± 13.88 | 46.28 ± 9.64 | 48.49 ± 10.62 | 63.95 ± 10.21* | 54.72 ± 5.88 | 53.10 ± 7.58 |
| LV Vol; s (uL) | 7.55 ± 3.03 | 12.11 ± 5.18 | 8.00 ± 3.36 | 20.99 ± 6.22** | 8.77 ± 2.51 | 17.74 ± 4.90** |
| Heart Rate (BMP) | 557 ± 30 | 548 ± 23 | 572 ± 17 | 542 ± 26* | 559 ± 15 | 573 ± 57 |

*$P < 0.05$;
**$P < 0.01$.

Figure 2A:
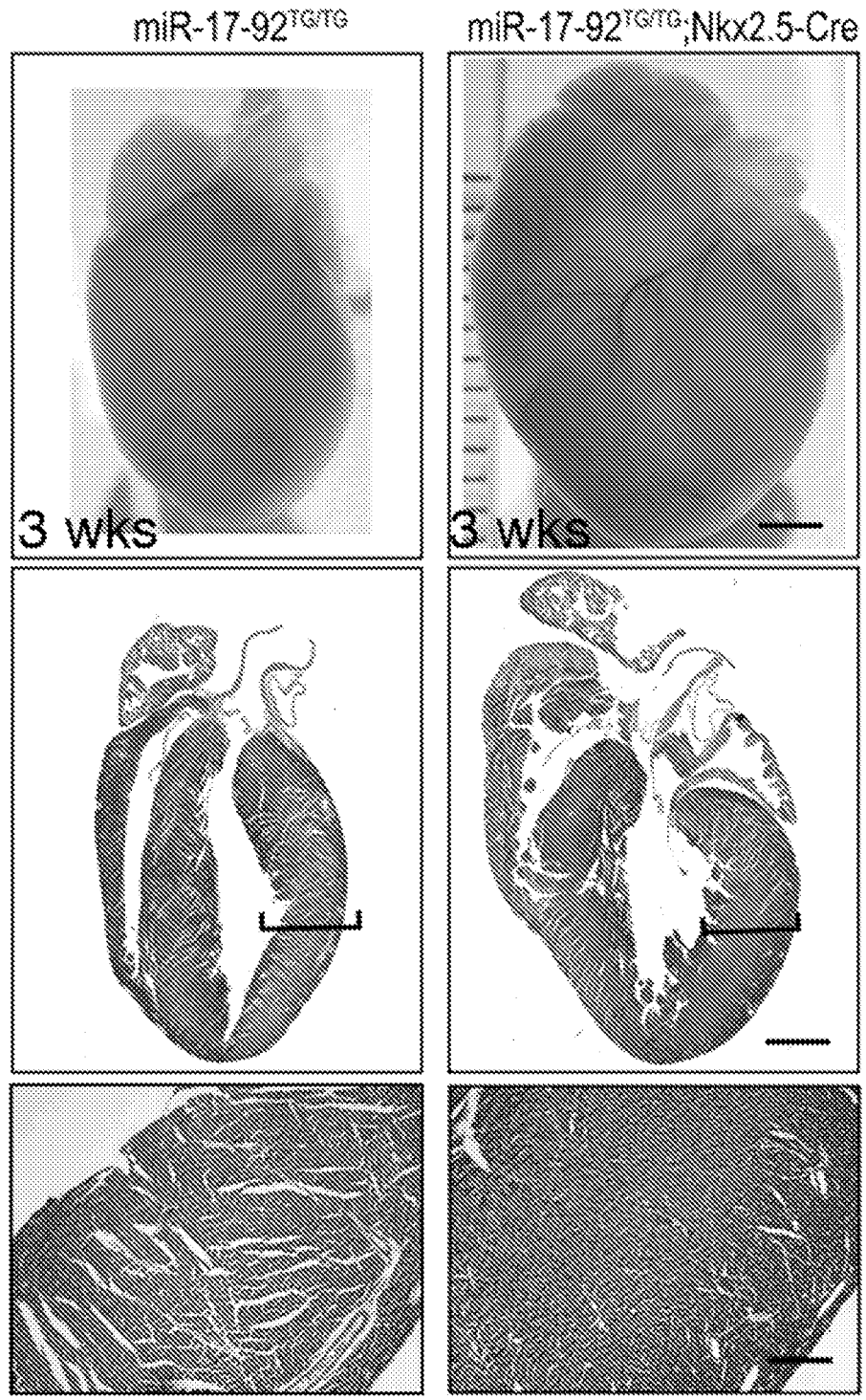
Figure 2B:
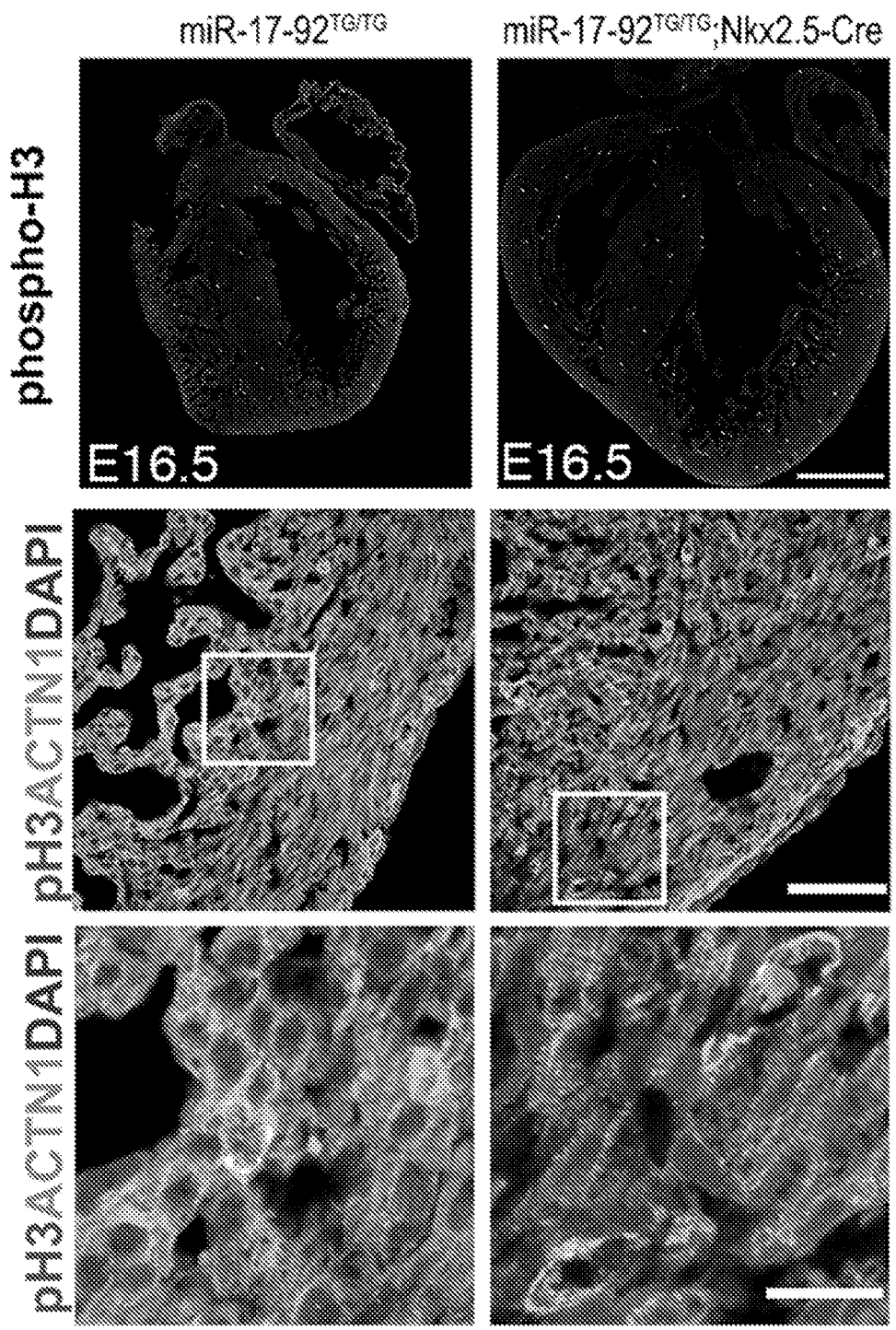
Figure 2C:
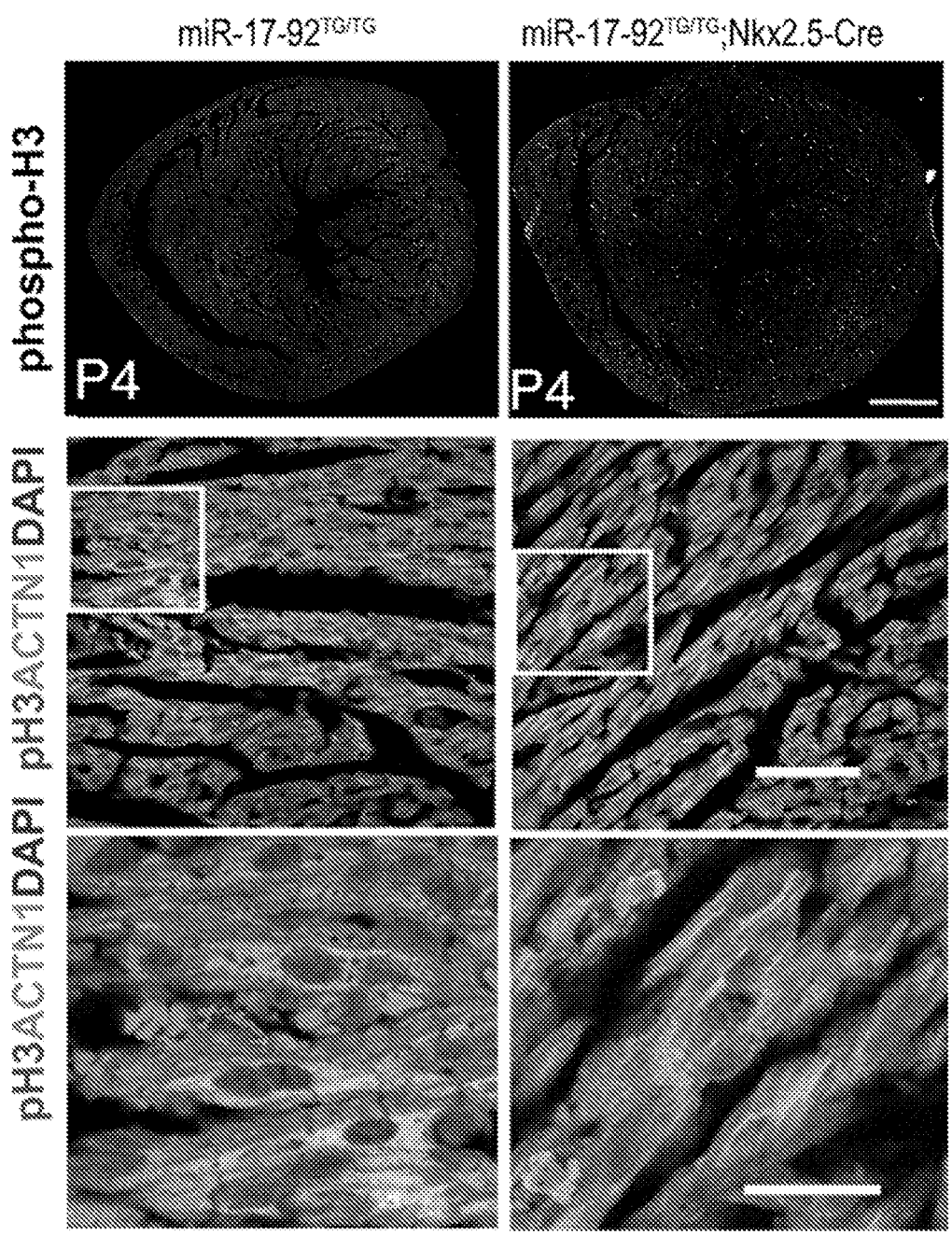
Figure 2F:
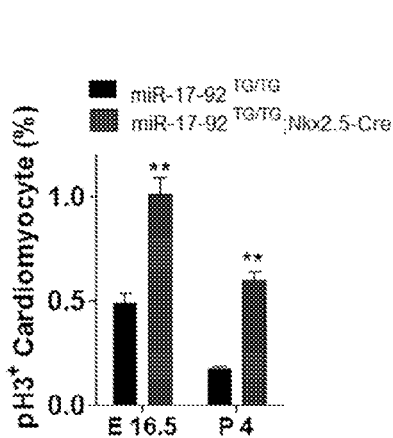
Figure 2F:
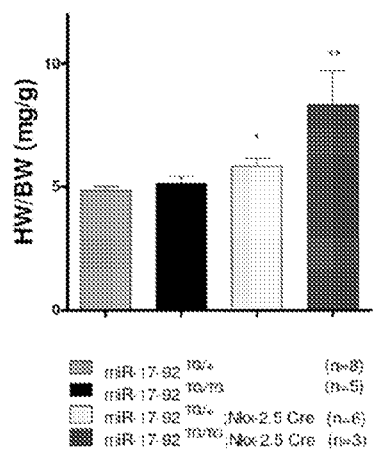
Figure 2F:
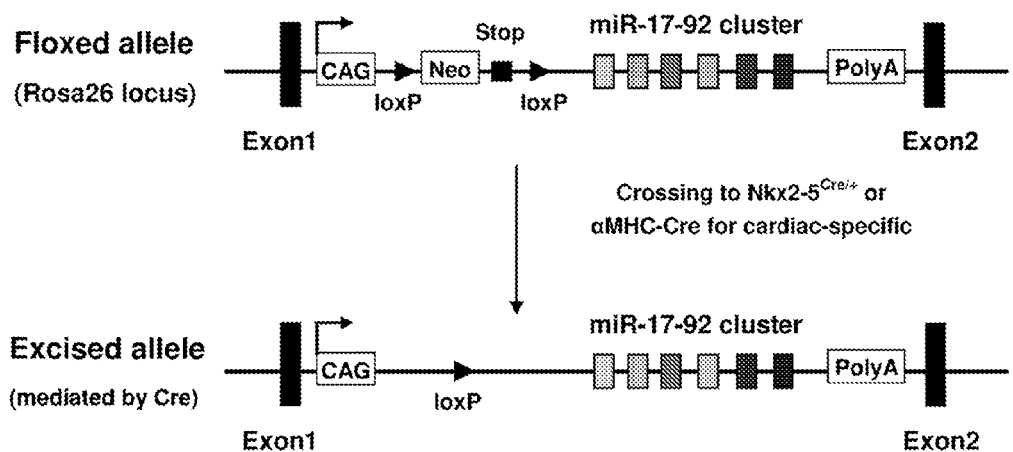

Example 2 miR-17-92 is Sufficient to Induce Cardiomyocyte Proliferation in Embryonic and Postnatal Hearts Having demonstrated that miR-17-92 is required for cardiomyocyte proliferation in embryonic and postnatal hearts, the next experiments tested whether overexpression of miR-17-92 was sufficient to induce cardiomyocyte proliferation. Cardiac-specific conditional transgenic mice were generated to overexpress miR-17-92 in the heart. The "foxed miR-17-92 knock-in allele", in which a loxP-flanked Neo-STOP cassette was inserted upstream of the bicistronic human miR-17-92 cluster and knocked into the Rosa26 locus (named miR-17-92-KI)[16], were first bred with the Nkx2.5-Cre mice to achieve the overexpression of miR-17-92 in embryonic and postnatal hearts (FIG. 2f, g). The hearts of cardiac-specific miR-17-92 transgenic mice (named miR-17-92-TG$^{nkx2.5}$) were dramatically enlarged (FIG. 2a). Histological section revealed that the ventricle wall was substantially thickened in the hearts of miR-17-92-TG$^{nkx2.5}$ mice (FIG. 2a). The heart showed hyperplasia and the trabeculae were highly condensed and packed (FIG. 2a, lower panels). There was no evidence of cardiomyocyte hypertrophy (FIG. 2a). The increase of cardiomyocyte numbers resulted from an increase in cardiomyocyte proliferation. Phosphorylated histone H3 was used to mark proliferating cardiomyocytes, and overexpression of miR-17-92 was shown to be sufficient to enhance cardiomyocyte proliferation in both embryonic and postnatal hearts (FIG. 2b, c, d). Concordantly, there was a significant increase in heart/body weight ratios in the miR-17-92-TG$^{nkx2.5}$ mice (FIG. 2e).

Figures 2G, 2H:
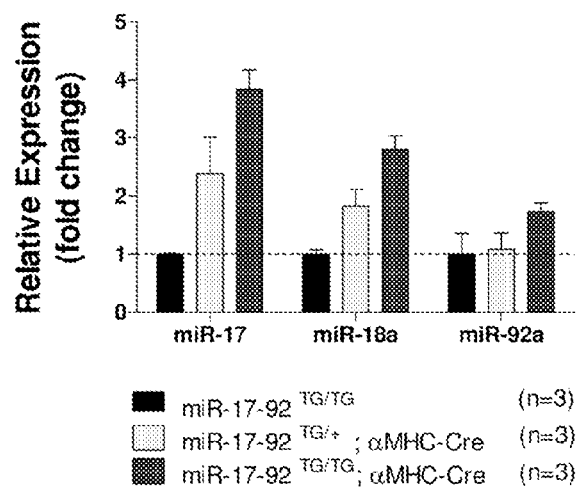

Next, transgenic mice were generated to overexpress miR-17-92 predominantly in postnatal and adult cardiomyocytes. The miR-17-92-KI mice were bred with alpha-MHC-Cre transgenic mice, in which the expression of Cre recombinase was directed by the cardiac-specific alpha-MHC (Myh6) promoter, to generate cardiac-specific miR-17-92 transgenic mice (named miR-17-92-TG$^{MHC}$). About a 2-5 fold increase in miR-17-92 expression was observed in the transgenic hearts (FIG. 2h). Most miR-17-92-TG$^{MHC}$ mice survived to adulthood without overt abnormality (Table 2).

TABLE 2

Genotyping results of weaning age mice from intercrossing of miR-17-92$^{Tg/TG}$ and miR-17-92$^{TG/+}$; αMHC-Cre mice.

| | Genotypes | | | | |
|---|---|---|---|---|---|
| | miR17-92$^{TG/+}$ | miR17-92$^{TG/+}$; αMHC-Cre | miR17-92$^{TG/TG}$ | miR17-92$^{TG/TG}$; αMHC-Cre | Total |
| Number | 49 | 59 | 58 | 43 | 209 |
| Percentage | 23.4% | 28.2% | 27.8% | 20.6% | 100% |

Figure 3J:
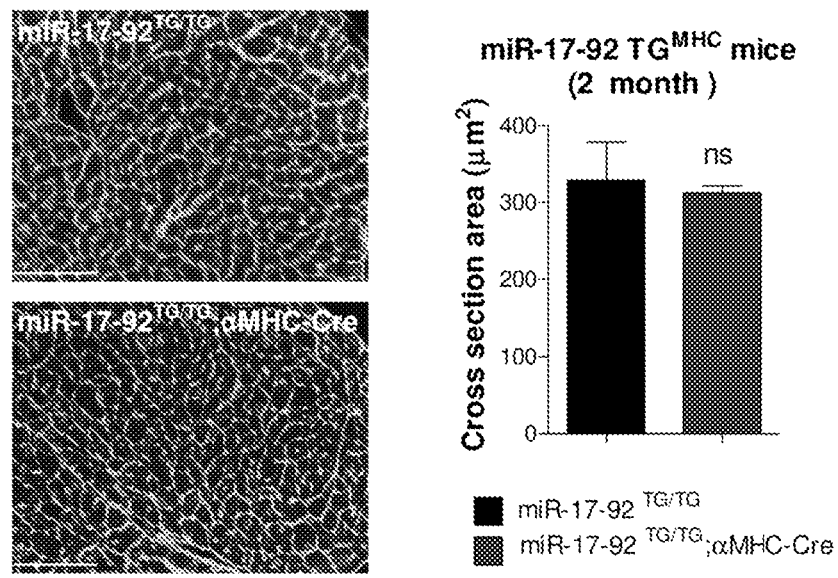
Figure 3K:
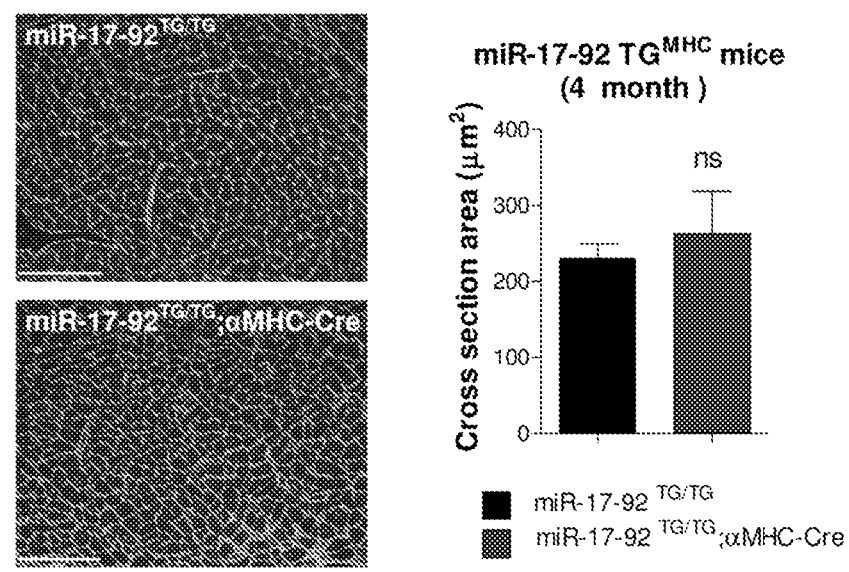

The hearts of the miR-17-92-TG$^{MHC}$ mice were substantially enlarged (FIG. 3a), and the heart/body weight ratio was significantly increased in these mice (FIG. 3b). Quantitative measurement of cardiomyocyte cell size and cell number of the miR-17-92-TG$^{MHC}$ hearts demonstrated a substantial increase in the cell number in the heart of miR-17-92-TG$^{MHC}$ mice, whereas the size of cardiomyocyte was not changed (FIGS. 3j, k). Cardiomyocytes were isolated from adult hearts using the Langendorf isolation method; there was substantial increase in total cardiomyocyte numbers in miR-17-92-TG$^{MHC}$ hearts (FIG. 3c, d). Intriguingly, there was an increase in total numbers of mono-nucleus cardiomyocytes and a decrease in bi-nuclei cardiomyocytes in miR-17-92-TG$^{MHC}$ hearts (FIG. 3e). Consistent with the increase in the cell numbers, the proliferation of cardiomyocytes, marked by phosphorylated histone H3 (pH3), was enhanced in miR-17-92-TG$^{MHC}$ hearts (FIG. 3f, g). Increased cell proliferation in miR-17-92-TG$^{MHC}$ hearts was further confirmed by 5-ethynyl-2'-deoxyuridine (EdU) incorporation and quantification (FIG. 3h, i).

Figure 4A:
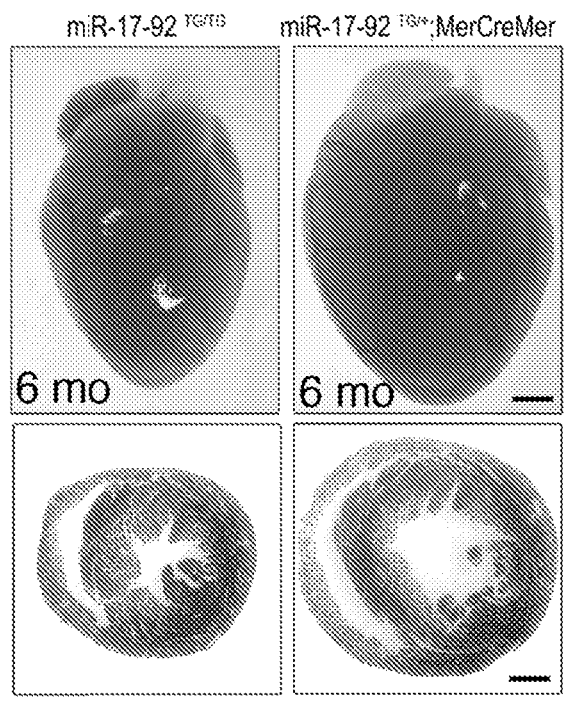
Figure 4B:
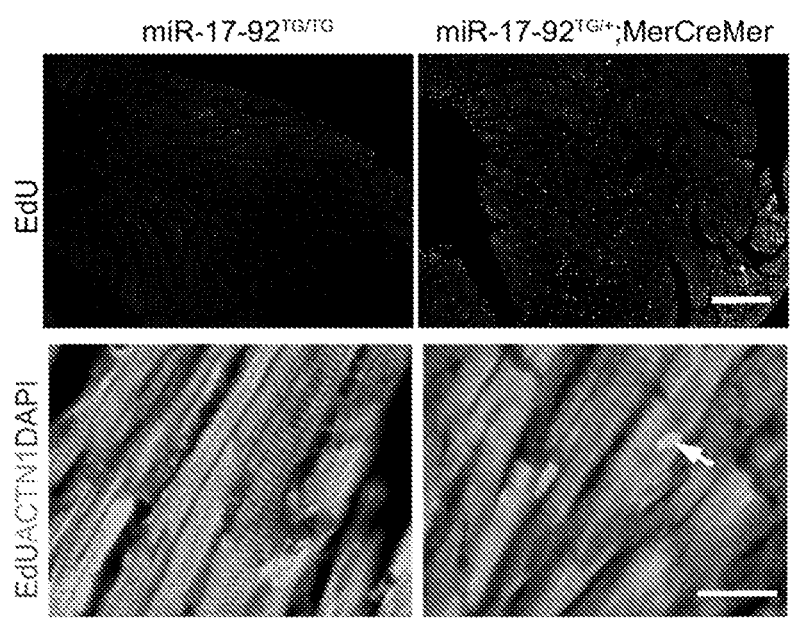
Figure 4F:
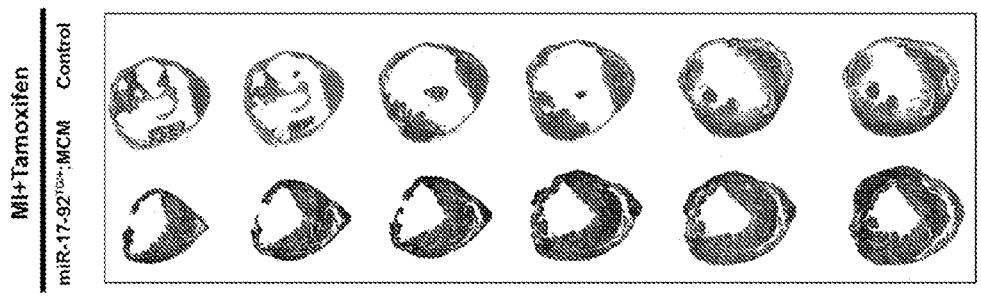
Figure 4G:
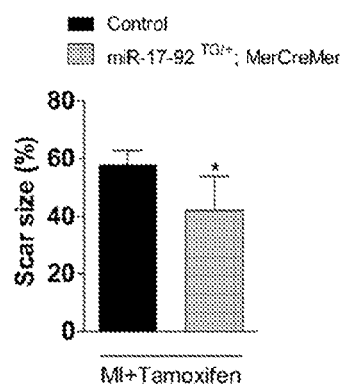
Figure 4H:
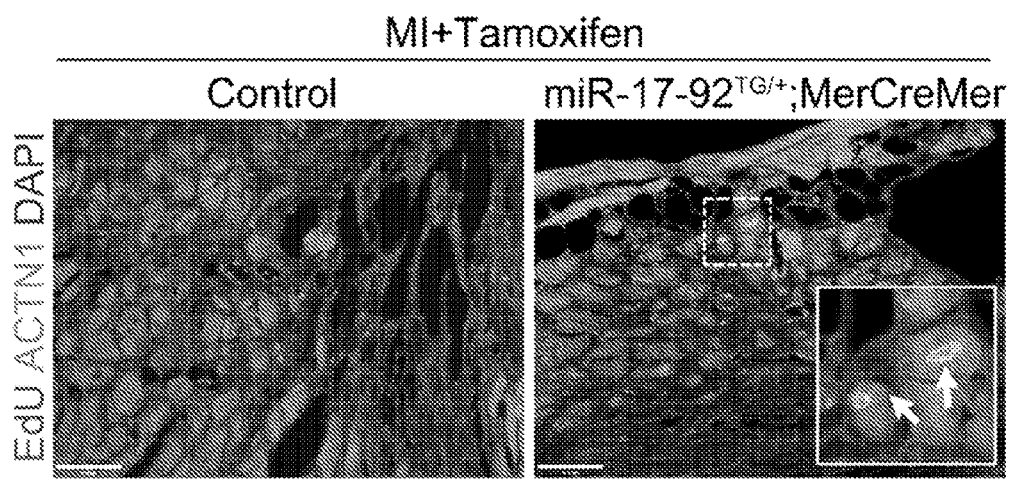
Figure 4I:
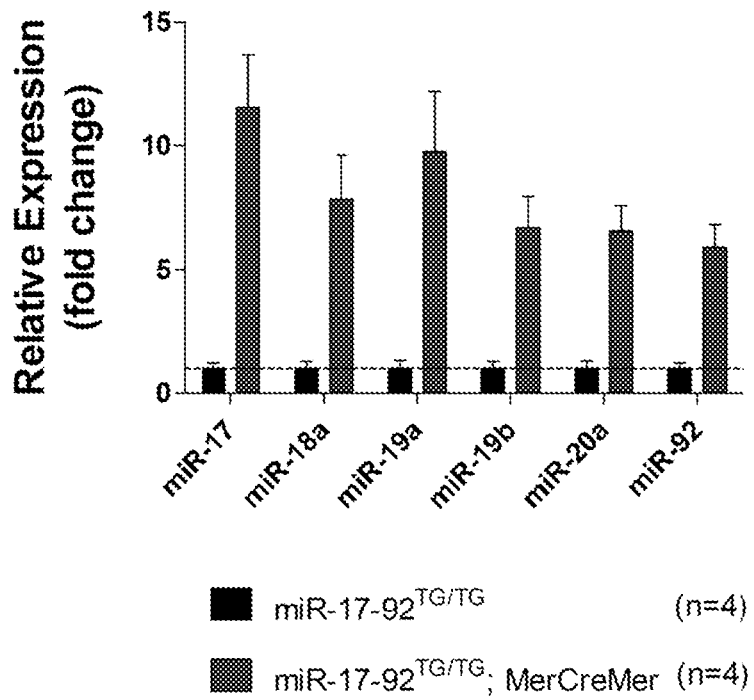

Example 3 miR-17-92 Induces Cardiomyocyte Proliferation in Adult Hearts and in Response to Injury The above data indicate that overexpression of miR-17-92 was sufficient to induce cardiomyocyte proliferation in embryonic, neonatal and adult hearts. To further determine the function of miR-17-92 in the proliferation of postmitotic cardiomyocytes in adult hearts more definitely, an inducible system was utilized to overexpress miR-17-92 in cardiomyocytes of four-month-old mice. The miR-17-92-KI mice were bred with alpha-MHC-MerCreMer transgenic mice in which the Myh6 promoter directs the expression of a tamoxifen-inducible Cre recombinase in cardiomyocytes. miR-17-92 overexpression was induced in adult cardiomyocytes by activating tamoxifen-inducible Cre recombinase. Cardiac-specific overexpression of members of the miR-17-92 cluster was confirmed in the hearts of miR-17-92 transgenic mice (named miR-17-92-TG$^{MerCreMer}$) after tamoxifen administration (FIG. 4i). The hearts of miR-17-92-TG$^{MerCreMer}$ mice were substantially larger than that of the littermate controls after miR-17-92 overexpression (FIG. 4a). Tissue sections revealed an increase in wall thickness and left ventricle dimension (FIG. 4a). Whether overexpression of miR-17-92 in adult cardiomyocytes could induce cell proliferation was also examined. Using EdU incorporation assay, a marked increase in the EdU incorporation in the cardiomyocytes of six-month old miR-17-92-TG$^{MerCreMer}$ hearts was found (FIG. 4b). Cardiomyocytes from the hearts of miR-17-92-TG$^{MerCreMer}$ and control mice were isolated to determine the total numbers of cardiomyocytes, and overexpression of miR-17-92 substantially increased total cardiomyocyte number in adult hearts (FIG. 4c). Quantitative measurement of the size of isolated adult cardiomyocytes showed that the size of cardiomyocytes was reduced in the heart of miR-17-92-TG$^{MerCreMer}$ mice (FIG. 4d).

To test whether this cluster of miRNAs is involved in the regulation of cardiomyocyte proliferation and cardiac repair in response to injury, myocardial infarction (MI) was induced by coronary artery occlusion (FIG. 4e). MI results in massive cardiomyocyte death, cardiac hypertrophy, fibrosis and cardiac remodeling. Overexpression of miR-17-92 in adult cardiomyocytes modestly protected the heart from MI-induced injury (FIG. 4f). Quantification confirmed the decrease in the size of scar in the hearts of miR-17-92-TG$^{MerCreMer}$ mice after MI (FIG. 4g). Using EdU incorporation assay, a marked increase in the EdU incorporation in the cardiomyocytes of border zone of miR-17-92-TG$^{MerCreMer}$ hearts was found (FIG. 4h). Similarly, both miR-17-92 transgenic and control mice were treated with doxorubicin, a cancer drug that can cause heart failure as side-effect, to induce stress. Overexpression of miR-17-92 modestly induced cardiomyocyte proliferation upon doxorubicin treatment.

Example 4 miR-17-92 is Sufficient to Induce Neonatal Cardiomyocyte Proliferation In Vitro

To test whether members of this cluster of miRNAs play a similar role in cardiomyocyte proliferation in vitro, neonatal rat cardiomyocytes were transfected with mimics or inhibitors of each member of the miR-17-92 cluster and cardiomyocyte proliferation assayed[17,18]. Cardiomyocytes isolated from postnatal day 1 (P1) hearts, in which cardiomyocytes are still undergoing active proliferation, were used[7]. The following miR-17-92 mimic and inhibitor target sequences were used:

| MIRIDIAN Mimic and Hairpin inhibitor target sequences | SEQ ID NO: |
|---|---|
| miR-17: CAAAGUGCUUACAGUGCAGGUAG | 6 |
| miR-18a: UAAGGUGCAUCUAGUGCAGAUAG | 8 |
| miR-19a: UGUGCAAAUCUAUGCAAAACUGA | 1 |
| miR-19b: UGUGCAAAUCCAUGCAAAACUGA | 3 |
| miR-20a: UAAAGUGCUUAUAGUGCAGGUAG | 10 |
| miR-92a: UAUUGCACUUGUCCCGGCCUG | 12 |

After being transfected with the miR-17-92 mimics or inhibitors, the cell culture was then incubated with EdU to label DNA synthesis and cell proliferation. Indeed, miR-17-92 mimics, especially miR-19a/b family, potently induced cardiomyocyte proliferation (FIG. 5a). Conversely, inhibition of members of the miR-17-92 cluster, in particular miR-19a/b, substantially reduced cardiomyocyte proliferation, evidenced by the decrease of EdU signal and the reduction of total cardiomyocyte numbers when compared with controls (FIG. 5b). Furthermore, postnatal day 4 (P4) cardiomyocytes, in which cell proliferation starts to diminish, were treated with miR-17-92 mimics. The miR-17-92 mimics, miR-19a/b in particular, significantly induced EdU incorporation. This observation was further confirmed by quantitative analyses (FIG. 5h). The expression of cyclin-dependent kinase 1 (CDK1), a highly conserved serine/threonine kinase involved in cell cycle progression[19], was examined in miR-17-92 mimic treated cardiomyocytes. Consistent with the view that miR-17-92 induced cardiomyocyte proliferation, miR-17-92 induced the expression of CDK1 in cardiomyocytes (FIG. 5c).

Next, neonatal cardiomyocytes were isolated from miR-17-92-KI mice. Cultured cardiomyocytes were infected with ad-cTNT-Cre to induce the overexpression of miR-17-92. Overexpression of miR-17-92 in mouse neonatal cardiomyocytes, but not the cells treated with the control Ad-lacZ, dramatically enhanced the incorporation of EdU, indicating an increase in cardiomyocyte proliferation (FIG. 5d).

Together, these data demonstrate that miR-17-92 mimics induce, while miR-17-92 inhibitors reduce cardiomyocyte proliferation in vitro and ex vivo.

Example 5 miR-17-92 Represses PTEN to Induce Cardiomyocyte Proliferation

The expression of putative miR-17-92 targets that are known to play a role in cell proliferation was tested[20]. It was reasoned that the expression of these targets might be inversely correlated with the expression of miR-17-92, which is decreased in the hearts of miR-17-92-TG mice and increased in the hearts of miR-17-92-KO mice. Indeed, the expression of several targets was elevated in the hearts of miR-17-92-KO mice (FIG. 5e), and repressed in the hearts of miR-17-92-TG mice (FIG. 5f). The experiments focused on PTEN, a tumor suppressor and a member of family of protein tyrosine phosphatases[21-23], which was most dramatically altered in the hearts of miR-17-92 transgenic and mutant mice (FIG. 5e, f). PTEN has been supposed to be a direct target of miR-19a/b[24], the most potent member of the miR-17-92 cluster to induce tumor growth[24] and to promote cardiomyocyte proliferation in the present study (FIG. 5a, b). Deletion of PTEN leads to axon regeneration in the central neural system, further highlighting the role of PTEN in cell proliferation and regeneration[25]. The next experiments asked whether PTEN could mediate the function of miR-19a/b in cardiomyocyte proliferation, and more specifically, whether overexpression of PTEN could suppress miR-19a/b-induced cardiomyocyte proliferation. PTEN was overexpressed in neonatal rat cardiomyocyte using a modified RNA approach[26]. Dose-dependent overexpression of PTEN protein was achieved in transfected cells (FIG. 5i). Overexpression of PTEN completely abolished miR-19a/b-induced cardiomyocyte proliferation (FIG. 5g).

Example 6 miR17-92 Members Improved Cardiac Function in Post-Myocardial Infarction (MI) Hearts In Vivo The following experiments were performed to demonstrate the ability of miR-17-92 members, specifically miR-19a/b, oligonucleotides to repair diseased hearts after heart attack (myocardial infarction), or chronic heart failure, in an ischemic Injury Model-Myocardial infarction (MI) and a cardiac toxic model.

8 weeks old wild type C57BL/6 mice were randomly subjected to intra-cardiac injection of microRNA mimic miR-19a/19b or control mimics (10 ug per mouse), respectively, immediately after myocardium infarction (MI) surgery performed as described above.

Some of the mice were sacrificed at about 3 days after the surgery and mimic injection, and miR-19a expression levels were analyzed by real-time Q-PCR using whole heart tissue. The results, shown in FIG. 7A, demonstrate increased expression of miR-19a after intra-cardiac injection of miR-19a/19b mimics in post-MI hearts.

Echocardiography analyses of cardiac function were performed at 2 and 4 weeks post-MI surgery from miR-19a/19b and control groups. N of each group was indicated. The results, shown in shown in Table 3, demonstrate that left ventricular end diastolic posterior wall dimension (LVPW;d) and left ventricular end-systolic posterior wall dimension (LVPW;s) were increased. In contrast, both left ventricular end diastolic internal dimension (LVID;d) and left ventricular end systolic internal dimension (LVID;s) were reduced in miR-19a/b injected heart, indicating that miR-19a/b prevents the progress of cardiac dilation. In addition, FIG. 7B shows that intra-cardiac injection of miR-19a/19b miR-19a/19b mimics improved cardiac function post MI, as indicated by increases in left ventricular end diastolic posterior wall dimension and fractional shortening.

TABLE 3

Table 3. 8 weeks old wild type C57BL/6 mice were randomly subjected to intra-cardiac injection of microRNA mimic miR-19a/19b and control, respectively, after myocardium infarction (MI) surgery. Echocardiography analyses of cardiac function were performed at 2 and 4 weeks post-MI surgery from miR-19a/19b and control injected groups.

|  | 2-weeks-old | | 4-weeks-old | |
| --- | --- | --- | --- | --- |
|  | Control (N = 5) | miR-19a/19b (N = 10) | Control (N = 3) | miR-19a/19b (N = 2) |
| IVS; d (mm) | 0.478 ± 0.081 | 0.494 ± 0.070 | 0.438 ± 0.068 | 0.671 ± 0.038* |
| IVS; s (mm) | 0.531 ± 0.096 | 0.620 ± 0.076 | 0.501 ± 0.015 | 0.751 ± 0.076** |
| LVID; d (mm) | 4.915 ± 1.003 | 4.451 ± 0.646 | 5.205 ± 0.422 | 4.252 ± 0.778 |
| LVID; s (mm) | 3.971 ± 1.210 | 3.150 ± 0.685 | 4.150 ± 0.430 | 3.045 ± 0.854 |
| LVPW; d (mm) | 0.478 ± 0.052 | 0.580 ± 0.031** | 0.492 ± 0.031 | 0.590 ± 0.038* |
| LVPW; s (mm) | 0.671 ± 0.083 | 0.832 ± 0.155 | 0.581 ± 0.031 | 0.724 ± 0.000** |
| EF (%) | 40.99 ± 15.49 | 56.65 ± 9.60** | 41.16 ± 6.137 | 55.82 ± 11.37 |
| FS (%) | 20.49 ± 8.80 | 29.80 ± 6.63** | 20.33 ± 3.451 | 29.04 ± 7.10 |
| LV Mass (mg) | 88.22 ± 24.90 | 84.61 ± 15.38 | 95.01 ± 14.65 | 96.71 ± 30.26 |
| LV Mass (Corrected, mg) | 70.58 ± 19.92 | 67.69 ± 12.30 | 76.01 ± 11.72 | 77.37 ± 24.21 |
| LV Vol; d (uL) | 119.07 ± 57.29 | 92.33 ± 31.23 | 130.59 ± 23.71 | 82.93 ± 34.95 |
| LV Vol; s (uL) | 76.56 ± 53.64 | 41.82 ± 20.26* | 77.19 ± 18.80 | 38.63 ± 24.87 |
| Heart Rate (BMP) | 634 ± 19 | 627 ± 24 | 612 ± 46 | 657 ± 12* |

N of each group was indicated.
*$P < 0.05$;
**$P < 0.01$ vs control group.
IVS; d: Interventricular septal thickness at diastole;
IVS; s Interventricular septal thickness at systole;
LVID; d: Left ventricular end diastolic internal dimension;
LVID; s: Left ventricular end systolic internal dimension;
LVPW; d: Left ventricular end diastolic posterior wall dimension;
LVPW; s: Left ventricular end systolic posterior wall dimension;
EF: Ejection fraction;
FS: Fractional shortening;
LV Vol; d: Left ventricular end diastolic volume.
LV Vol; s: Left ventricular end systolic volume.

Mice were sacrificed at 2 weeks, or 4 weeks after surgery and histology and immunohistology were examined Fast green collagen staining was used to mark the myocardium and Sirius red was used to visualize scar tissue. As shown in FIGS. 7B-7E, intra-cardiac injection of miR-19a/19b miR-19a/19b mimics preserves cardiac function, prevents cardiac dilation, reduces infarct size, and enhances survival after MI in mice.

In addition, mice are sacrificed at 4 months, 6 months, 8 months, 9 months, 10 months, and/or a year after surgery, and the expression of cardiac marker genes, including ANF, BNP, cTNT, fetal and adult MHC, is examined using quantitative RT-PCR and/or Western blots.

Example 7 miR17-92 Members Stimulate Cardiomyocyte Proliferation and Cardiac Regeneration In Vivo in a Cardiac Toxic Model The following experiments are performed to demonstrate the ability of miR-17-92 members, specifically miR-19a/b, oligonucleotides to repair diseased hearts in a cardiac toxic model.

Cardiac Toxic Model

Doxorubicin (trade name, Adriamycin) is an anthracycline antibiotic used in cancer chemotherapy. Doxorubicin treatment can produce a dose dependent dilated phenotype and heart failure over time after sufficient myocardial injury and cell death. 2-4 months old male C57 mice will be used. After the mice receive subcutaneously buprenorphine (0.05 mg/kg) to provide analgesia, adult mice receive doxorubicin (2 intraperitoneal (i.p.) injections of 10 mg/kg at 3-day intervals, 20 mg/kg cumulative dose). Control animals are treated with only buprenorphine and i.p. saline. The mice are euthanized with carbon dioxide on days 1, 7, and 14 after the last injection of doxorubicin.

All mice are given a single dose of 5 µg synthetic microRNA-19a/b (Dharmacon, Lafayette, Colo.) formulated with NLE according to the manufacturer's instructions by intra-myocardium injection. The NLE (MaxSuppressor in vivo RNALancerII) is purchased from BIOO Scientific, (Austin, Tex.). NLE consists of 1,2-dioleoyl-sn-glycero-3-phosphocholine, squalene oil, polysorbate 20, and an antioxidant that—in complex with synthetic miRNAs—forms nanoparticles in the nanometer diameter range.

Cardiac function is analyzed by echocardiography measurement at 1, 2 and 4 weeks after treatment. Mice are sacrificed about 4 weeks, 4 months, 6 months, 8 months, 9 months, 10 months, and/or a year after final injection and histology, immunohistology will be examined. The expression of cardiac marker genes, including ANF, BNP, cTNT, fetal and adult MHC, is examined using quantitative RT-PCR and/or Western blots.

Example 8

AAV Mediated Delivery of Mir-19a/B

In some experiments, an AAV-based vector system, an especially attractive platform, is used for miR-19a/b delivery. There are several advantages of using AAV delivery system: 1) when delivered in viral vectors, miRNAs are continually transcribed, allowing sustained high level expression in target tissues. 2) The use of cardiac tissue-specific promoters could restrict this expression to the heart (for example, the availability of multiple AAV serotypes, especially AAV9, allows the expression of miRNAs predominantly in myocardium of the heart). 3) AAV carry substantially diminished risk of insertional mutagenesis since viral genomes persist primarily as episomes and the general safety of AAV has been well documented, with clinical trials using this platform already under way.

In these experiments, an AAV vector is generated to express precursors of miR-19a/b (i.e., SEQ ID NO:2 or 4). AAV is administered at a dose of $10^{12}$ vg per mouse by tail vein injection (200 µl total volume) using a 30 gauge ultra-fine insulin syringe. AAV-miR-19a/b is delivered in mice with myocardial infarction surgery and in aged mice with chronically heart failure (>18 months old).

Example 9

Using an AAV-9 System to Specifically Deliver miR-19a/19b into the Heart

AAV is an ideal gene therapy vector for in vivo gene transfer because its low immunogenicity favors persistent transgene expression (Wright, et al., Basic Res. Cardiol. 96, 227-236 (2001)). AAV vector of serotype 9 has significant cardiac tropism (Zincarelli et al., Mol Ther 16, 1073-1080 (2008)). AAV9 was used to specifically deliver miR-19a/19b in the heart to test the therapeutic potential to repair infarcted hearts.

AAV9-miR-19a/19b Cloning and Virus Packaging.

AAV9-cTNT::miR-19a/19b was generated in which the cardiac specific TNNT2 promoter was used to drive the expression of miR-19a/19b in the heart. An AAV9-cTNT::Luciferase (AAV9-Luc) and an AAV9-cTNT::eGFP was used as a negative control.

Mouse miR-19a/19b precursor sequences and the luciferase gene were cloned into the AAV Inverted Terminal Repeat (ITR)-containing plasmid, downstream of the rat cardiac specific TNNT2 promoter, to generate pEn.cTnT::miR-19a/19b and pEn.cTnT::Luciferase, respectively. To package AAV9, the AAV plasmids were co-transfected into HEK293T cells together with AAV9-Rep-Cap and pHelper (pAd deltaF6). Three days later, cells were collected and lysed. AAV was purified by gradient centrifugation and the titer of AAV viruses determined.

The function of miR-19a/19b is tested in ischemic heart disease in two experimental settings, which are schematically illustrated in FIG. 8.

Example 9.1

Neonatal mice (post-natal day 1 or 3) are intraperitoneally or subcutaneously injected with AAV9-Luc(AAV9-control), AAV9-cTNT::eGFP and AAV9-miR-19a/19b at a dose of $1 \times 10^{12}$ viral genome particles per animal, using an insulin syringe with incorporated 30-gauge needle. Eight weeks after AAV injection, the mice are subjected to myocardial infarction (MI) surgery by permanent left anterior descending (LAD) coronary artery ligation. Echocardiography is further performed to document cardiac function at different time points (2, 3, or 4 weeks, 2, 4 and 8 months).

Figure 9:
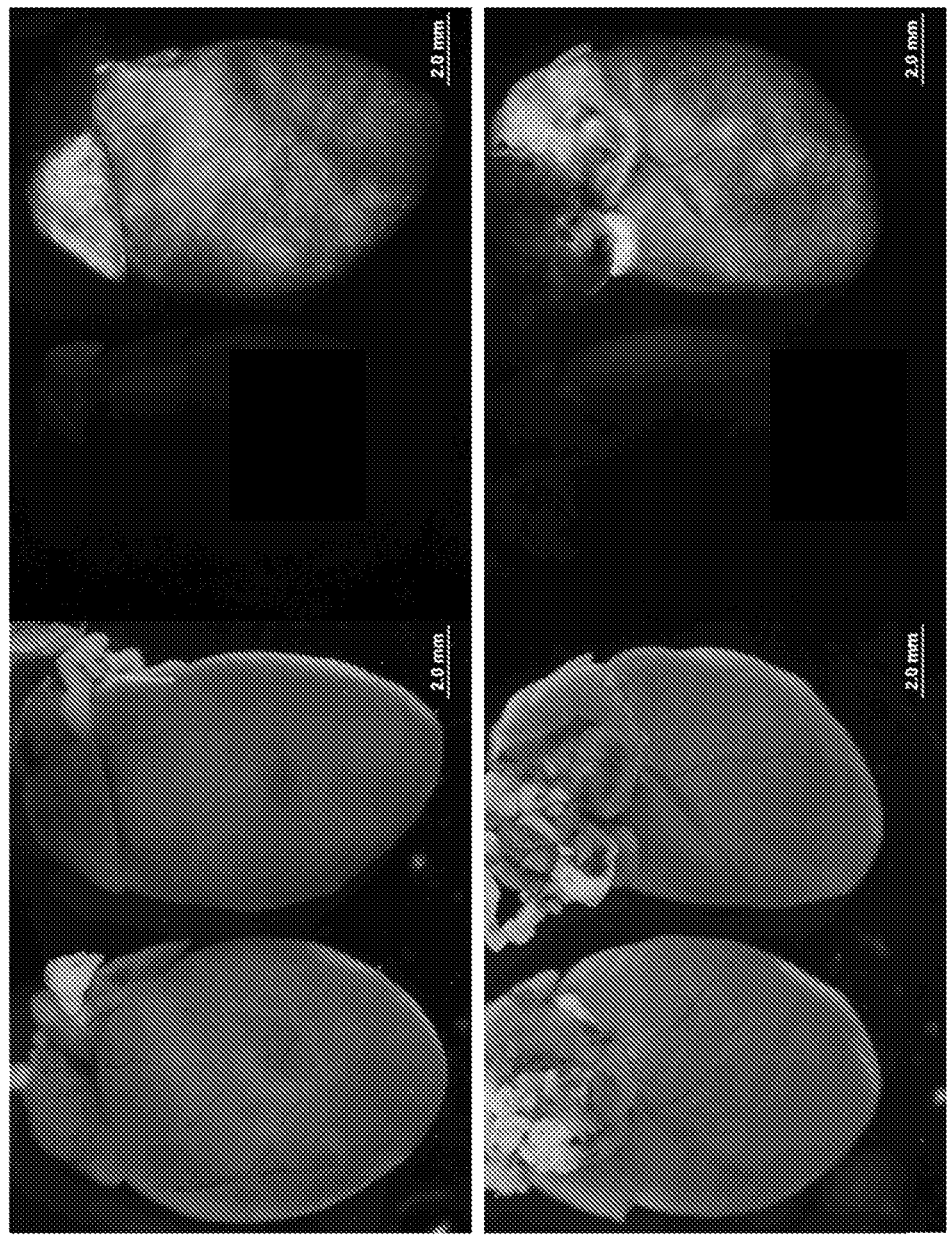

P1 mice were injected s.c. with the AAV9-Luc(AAV9-control) and AAV9-cTNT::eGFP control viruses and sacrificed three weeks later. As shown in FIG. 9, robust and uniform expression was obtained from the AAV9-cTNT::eGFP virus, while no significant expression was seen in the luciferase virus-treated animals.

Example 9.2

8 week old mice are used. After left anterior descending coronary artery ligation (MI surgery), AAV9-miR-9a/19b or AAV9-Luc (control) is injected into three different positions along the margin of the ischemic area in the heart. Heart function is measured echocardiographically as both fractional area change (FAC) and fractional shortening (FS) in the AAV9-miR-19a/19b group compared to AAV9-control group at 2 weeks, 4 weeks, 2, 4 and 8 months after MI.

Six week old adult mice were treated with direct cardiac injections of the AAV9-Luc(AAV9-control) and AAV9-cTNT::eGFP control viruses and sacrificed two weeks later. As can be seen in FIG. 10, no detectable expression was seen in the luciferase virus-treated animals, while areas of robust expression were seen in the animals administered the AAV9-cTNT::eGFP virus.

Thus, expression of a gene from an AAV vector can readily be obtained in adult cardiac tissues. It is expected that direct delivery of AAV-miR-19a/19b will significantly protect cardiac function in response to myocardial infarction.

REFERENCES

1. Kathiresan S, Srivastava D. Genetics of human cardiovascular disease. *Cell.* 2012; 148(6): 1242-1257.
2. Mudd J O, Kass D A. Tackling heart failure in the twenty-first century. *Nature.* 2008; 451(7181):919-928.
3. Poss K D, Wilson L G, Keating M T. Heart regeneration in zebrafish. *Science.* 2002; 298(5601):2188-2190.
4. Jopling C, Sleep E, Raya M, Marti M, Raya A, Izpisua Belmonte J C. Zebrafish heart regeneration occurs by cardiomyocyte dedifferentiation and proliferation. *Nature.* 2010; 464(7288):606-609.
5. Kikuchi K, Holdway J E, Werdich A A, Anderson R M, Fang Y, Egnaczyk G F, Evans T, Macrae C A, Stainier D Y, Poss K D. Primary contribution to zebrafish heart regeneration by gata4(+) cardiomyocytes. *Nature.* 2010; 464(7288):601-605.
6. Lepilina A, Coon A N, Kikuchi K, Holdway J E, Roberts R W, Burns C G, Poss K D. A dynamic epicardial injury response supports progenitor cell activity during zebrafish heart regeneration. *Cell.* 2006; 127(3):607-619.
7. Porrello E R, Mahmoud A I, Simpson E, Hill J A, Richardson J A, Olson E N, Sadek H A. Transient regenerative potential of the neonatal mouse heart. *Science.* 2011; 331(6020):1078-1080.
8. He L, Thomson J M, Hemann M T, Hernando-Monge E, Mu D, Goodson S, Powers S, Cordon-Cardo C, Lowe S W, Hannon G J, Hammond S M. A microRNA polycistron as a potential human oncogene. *Nature.* 2005; 435(7043): 828-833.
9. O'Donnell K A, Wentzel E A, Zeller K I, Dang C V, Mendell J T. c-Myc-regulated microRNAs modulate E2F1 expression. *Nature.* 2005; 435(7043):839-843.
10. Kasinski A L, Slack F J. Epigenetics and genetics. MicroRNAs en route to the clinic: progress in validating and targeting microRNAs for cancer therapy. *Nat Rev Cancer.* 2011; 11(12):849-864.
11. de Pontual L, Yao E, Callier P, Faivre L, Drouin V, Cariou S, Van Haeringen A, Genevieve D, Goldenberg A, Oufadem M, Manouvrier S, Munnich A, Vidigal J A, Vekemans M, Lyonnet S, Henrion-Caude A, Ventura A, Amiel J. Germline deletion of the miR-17 approximately 92 cluster causes skeletal and growth defects in humans. *Nat Genet.* 2011; 43(10):1026-1030.
12. Volinia S, Calin G A, Liu C G, Ambs S, Cimmino A, Petrocca F, Visone R, Iorio M, Roldo C, Ferracin M, Prueitt R L, Yanaihara N, Lanza G, Scarpa A, Vecchione A, Negrini M, Harris C C, Croce C M. A microRNA expression signature of human solid tumors defines cancer gene targets. *Proc Natl Acad Sci USA.* 2006; 103(7): 2257-2261.
13. Conkrite K, Sundby M, Mukai S, Thomson J M, Mu D, Hammond S M, MacPherson D. miR-17~92 cooperates with RB pathway mutations to promote retinoblastoma. *Genes Dev.* 2011; 25(16):1734-1745.
14. Mendell J T. miRiad roles for the miR-17-92 cluster in development and disease. *Cell.* 2008; 133(2):217-222.
15. Ventura A, Young A G, Winslow M M, Lintault L, Meissner A, Erkeland S J, Newman J, Bronson R T, Crowley D, Stone J R, Jaenisch R, Sharp P A, Jacks T. Targeted deletion reveals essential and overlapping functions of the miR-17 through 92 family of miRNA clusters. *Cell.* 2008; 132(5):875-886.
16. Xiao C, Srinivasan L, Calado D P, Patterson H C, Zhang B, Wang J, Henderson J M, Kutok J L, Rajewsky K. Lymphoproliferative disease and autoimmunity in mice with increased miR-17-92 expression in lymphocytes. *Nat Immunol.* 2008; 9(4):405-414.
17. Callis T E, Pandya K, Seok H Y, Tang R H, Tatsuguchi M, Huang Z P, Chen J F, Deng Z, Gunn B, Shumate J, Willis M S, Selzman C H, Wang D Z. MicroRNA-208a is a regulator of cardiac hypertrophy and conduction in mice. *J Clin Invest.* 2009; 119(9):2772-2786.
18. Tatsuguchi M, Seok H Y, Callis T E, Thomson J M, Chen J F, Newman M, Rojas M, Hammond S M, Wang D Z. Expression of microRNAs is dynamically regulated during cardiomyocyte hypertrophy. *J Mol Cell Cardiol.* 2007; 42(6):1137-1141.
19. Lee M G, Nurse P. Complementation used to clone a human homologue of the fission yeast cell cycle control gene cdc2. *Nature.* 1987; 327(6117):31-35.
20. Mestdagh P, Bostrom A K, Impens F, Fredlund E, Van Peer G, De Antonellis P, von Stedingk K, Ghesquiere B, Schulte S, Dews M, Thomas-Tikhonenko A, Schulte J H, Zollo M, Schramm A, Gevaert K, Axelson H, Speleman F, Vandesompele J. The miR-17-92 microRNA cluster regulates multiple components of the TGF-beta pathway in neuroblastoma. *Mol Cell.* 2010; 40(5):762-773.
21. Zheng H, Ying H, Yan H, Kimmelman A C, Hiller D J, Chen A J, Perry S R, Tonon G, Chu G C, Ding Z, Stommel J M, Dunn K L, Wiedemeyer R, You M J, Brennan C, Wang Y A, Ligon K L, Wong W H, Chin L, DePinho R A. p53 and Pten control neural and glioma stem/progenitor cell renewal and differentiation. *Nature.* 2008; 455 (7216):1129-1133.
22. Salmena L, Carracedo A, Pandolfi P P. Tenets of PTEN tumor suppression. *Cell.* 2008; 133(3):403-414.
23. Song M S, Salmena L, Pandolfi P P. The functions and regulation of the PTEN tumour suppressor. *Nat Rev Mol Cell Biol.* 2012; 13(5):283-296.
24. Olive V, Bennett M J, Walker J C, Ma C, Jiang I, Cordon-Cardo C, Li Q J, Lowe S W, Hannon G J, He L. miR-19 is a key oncogenic component of mir-17-92. *Genes Dev.* 2009; 23(24):2839-2849.
25. Sun F, Park K K, Belin S, Wang D, Lu T, Chen G, Zhang K, Yeung C, Feng G, Yankner B A, He Z. Sustained axon regeneration induced by co-deletion of PTEN and SOCS3. *Nature.* 2011; 480(7377):372-375.
26. Warren L, Manos P D, Ahfeldt T, Loh Y H, Li H, Lau F, Ebina W, Mandal P K, Smith Z D, Meissner A, Daley G Q, Brack A S, Collins J J, Cowan C, Schlaeger T M, Rossi D J. Highly efficient reprogramming to pluripotency and directed differentiation of human cells with synthetic modified mRNA. *Cell Stem Cell.* 2010; 7(5):618-630.

27. Rubart M, Field L J. Cardiac regeneration: repopulating the heart. *Annu Rev Physiol.* 2006; 68:29-49.
28. Ahuja P, Sdek P, MacLellan W R. Cardiac myocyte cell cycle control in development, disease, and regeneration. *Physiol Rev.* 2007; 87(2):521-544.
29. Bersell K, Arab S, Haring B, Kuhn B Neuregulin1/ErbB4 signaling induces cardiomyocyte proliferation and repair of heart injury. *Cell.* 2009; 138(2):257-270.
30. Hassink R J, Pasumarthi K B, Nakajima H, Rubart M, Soonpaa M H, de la Riviere A B, Doevendans P A, Field L J. Cardiomyocyte cell cycle activation improves cardiac function after myocardial infarction. *Cardiovasc Res.* 2008; 78(1):18-25.
31. Pasumarthi K B, Nakajima H, Nakajima H O, Soonpaa M H, Field U. Targeted expression of cyclin D2 results in cardiomyocyte DNA synthesis and infarct regression in transgenic mice. *Circ Res.* 2005; 96(1):110-118.
32. Soonpaa M H, Koh G Y, Pajak L, Jing S, Wang H, Franklin M T, Kim K K, Field U. Cyclin D1 overexpression promotes cardiomyocyte DNA synthesis and multinucleation in transgenic mice. *J Clin Invest.* 1997; 99(11):2644-2654.
33. Shan S W, Lee D Y, Deng Z, Shatseva T, Jeyapalan Z, Du W W, Zhang Y, Xuan J W, Yee S P, Siragam V, Yang B B. MicroRNA MiR-17 retards tissue growth and represses fibronectin expression. *Nat Cell Biol.* 2009; 11(8):1031-1038.
34. Bonauer A, Carmona G, Iwasaki M, Mione M, Koyanagi M, Fischer A, Burchfield J, Fox H, Doebele C, Ohtani K, Chavakis E, Potente M, Tjwa M, Urbich C, Zeiher A M, Dimmeler S. MicroRNA-92a controls angiogenesis and functional recovery of ischemic tissues in mice. *Science.* 2009; 324(5935):1710-1713.
35. Crackower M A, Oudit G Y, Kozieradzki I, Sarao R, Sun H, Sasaki T, Hirsch E, Suzuki A, Shioi T, Irie-Sasaki J, Sah R, Cheng H Y, Rybin V O, Lembo G, Fratta L, Oliveira-dos-Santos A J, Benovic J L, Kahn C R, Izumo S, Steinberg S F, Wymann M P, Backx P H, Penninger J M. Regulation of myocardial contractility and cell size by distinct PI3K-PTEN signaling pathways. *Cell.* 2002; 110(6):737-749.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a myocardial infarction or chronic heart failure in a subject, the method comprising:
   identifying and selecting a subject in need of treatment for a myocardial infarction or chronic heart failure; and
   administering to the selected subject a therapeutically effective amount of a microRNA (miR)-19a/19b oligonucleotide, wherein the miR-19a/b oligonucleotide comprises at least 18, 19, or 20 nucleotides with at least 80% identity to SEQ ID NO:1 or 3, including a region with 100% identity to nucleotides 1-8 of SEQ ID NO:1 or 3.

2. The method of claim 1, wherein the subject is over 65 years of age.

3. The method of claim 1, wherein the therapeutically effective amount is an amount sufficient to induce cardiomyocyte proliferation.

4. The method of claim 3, wherein the cardiomyocyte proliferation is sufficient to improve cardiac function, increase cardiac contractile force, or increase the thickness of the myocardium; and wherein the method optionally includes detecting an improvement in cardiac function, an increase in cardiac contractile force, or an increase in the thickness of the myocardium.

5. The method of claim 1, wherein the miR-19a/b oligonucleotide is a single stranded DNA or RNA that is at least 18, 19, or 20 nucleotides long, but less than 24 nucleotides long, and is identical to at least 18, 19, or 20 nucleotides of SEQ ID NO:1 or 3.

6. The method of claim 5, wherein the miR-19a/b oligonucleotide comprises at least one modification selected from the group consisting of: 5'-phosphorylation; at least one 2'-fluoro ribose modification; and a cholesterol moiety.

7. The method of claim 5, wherein the miR-19a/b oligonucleotide comprises SEQ ID NO:1 or 3.

8. The method of claim 1, wherein the miR-19a/b oligonucleotide is a double stranded DNA or RNA, comprising:
   a first strand comprising a sequence that is at least 80% identical to 18, 19, or 20 consecutive nucleotides of SEQ ID NO:1 or 3, with 100% identity to nucleotides 1-8 of SEQ ID NO:1 or 3;
   a second strand comprising a sequence that is complementary to the first strand; and
   an optional linker therebetween.

9. The method of claim 8, wherein the double stranded DNA or RNA comprises SEQ ID NO:2 or 4.

10. The method of claim 8, wherein the double stranded DNA or RNA comprises at least one modification selected from the group consisting of: 5'-phosphorylation; and 2'-O-methyl ribosyl substitution at position 2 in the first strand.

11. The method of claim 1, wherein the miR-19a/b oligonucleotide is administered locally to the heart of the subject.

12. The method of claim 1, wherein the miR-19a/b oligonucleotide is administered via a viral vector; a nanoparticle or microparticle; or a gelfoam.

13. The method of claim 1, wherein the subject is a post-neonatal, adolescent, or adult mammal.

14. The method of claim 13, wherein the subject is a human.

15. A method of reducing the risk of developing chronic heart failure in a subject, the method comprising:
   identifying and selecting a subject on the basis that they are at risk for chronic heart failure; and
   administering to the selected subject a therapeutically effective amount of a microRNA (miR)-19a/19b oligonucleotide, wherein the miR-19a/b oligonucleotide comprises at least 18, 19, or 20 nucleotides with at least 80% identity to SEQ ID NO: 1 or 3, including a region with 100% identity to nucleotides 1-8 of SEQ ID NO: 1 or 3.

16. The method of claim 15, wherein the subject is over 65 years of age; does not yet have chronic heart failure; or has not yet had a myocardial infarction.

17. The method of claim 15, wherein the therapeutically effective amount is an amount sufficient to induce cardiomyocyte proliferation.

18. The method of claim 17, wherein the cardiomyocyte proliferation is sufficient to improve cardiac function, increase cardiac contractile force, or increase the thickness of the myocardium; and wherein the method optionally includes detecting an improvement in cardiac function, an increase in cardiac contractile force, or an increase in the thickness of the myocardium.

19. The method of claim 15, wherein the miR-19a/b oligonucleotide is a single stranded DNA or RNA that is at least 18, 19, or 20 nucleotides long, but less than 24 nucleotides long, and is at least 80% identical to SEQ ID NO:1 or 3, with 100% identity to nucleotides 1-8 of SEQ ID NO:1 or 3.

20. The method of claim 19, wherein the miR-19a/b oligonucleotide comprises at least one modification selected from the group consisting of: 5'-phosphorylation; at least one 2'-fluoro ribose modification; and a cholesterol moiety.

21. The method of claim 19, wherein the miR-19a/b oligonucleotide comprises SEQ ID NO:1 or 3.

22. The method of claim 15, wherein the miR-19a/b oligonucleotide is a double stranded DNA or RNA, comprising:
   a first strand comprising a sequence that is at least 80% identical to 18, 19, or 20 consecutive nucleotides of SEQ ID NO:1 or 3, with 100% identity to nucleotides 1-8 of SEQ ID NO:1 or 3;

a second strand comprising a sequence that is complementary to the first strand; and an optional linker therebetween.

23. The method of claim 22, wherein the double stranded DNA or RNA comprises SEQ ID NO:2 or 4.

24. The method of claim 22, wherein the double stranded DNA or RNA comprises at least one modification selected from the group consisting of: 5'-phosphorylation; and 2'-O-methyl ribosyl substitution at position 2 in the first strand.

25. The method of claim 15, wherein the miR-19a/b oligonucleotide is administered locally to the heart of the subject.

26. The method of claim 15, wherein the miR-19a/b oligonucleotide is administered via a viral vector; a nanoparticle or microparticle; or a gelfoam.

27. The method of claim 15, wherein the subject is a post-neonatal, adolescent, or adult mammal.

28. The method of claim 27, wherein the subject is a human.

* * * * *

UNITED STATES PATENT AND TRADEMARK OFFICE
CERTIFICATE OF CORRECTION

| | |
|---|---|
| PATENT NO. | : 9,562,229 B2 |
| APPLICATION NO. | : 14/766505 |
| DATED | : February 7, 2017 |
| INVENTOR(S) | : Da-Zhi Wang and Jinghai Chen |

It is certified that error appears in the above-identified patent and that said Letters Patent is hereby corrected as shown below:

On the Title Page

Item (54) and in the Specification, Column 1, Line 1, delete "INCLUDING" and insert -- INDUCING --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

```
SEQUENCE LISTING

<160> NUMBER OF SEQ ID NOS: 20

<210> SEQ ID NO 1
<211> LENGTH: 23
<212> TYPE: RNA
<213> ORGANISM: Homo sapiens

<400> SEQUENCE: 1
ugugcaaauc uaugcaaaac uga                                            23

<210> SEQ ID NO 2
<211> LENGTH: 82
<212> TYPE: RNA
<213> ORGANISM: Homo sapiens

<400> SEQUENCE: 2
gcaguccucu guuaguuuug cauaguugca cuacaagaag aauguaguug ugcaaaucua    60
ugcaaaacug augguggccu gc                                             82

<210> SEQ ID NO 3
<211> LENGTH: 23
<212> TYPE: RNA
<213> ORGANISM: Homo sapiens

<400> SEQUENCE: 3
ugugcaaauc caugcaaaac uga                                            23

<210> SEQ ID NO 4
<211> LENGTH: 87
<212> TYPE: RNA
<213> ORGANISM: Homo sapiens

<400> SEQUENCE: 4
cacuguucua ugguuaguuu ugcagguuug cauccagcug ugugauauuc ugcugugcaa    60
auccaugcaa aacugacugu gguagug                                        87
```

```
<210> SEQ ID NO 5
<211> LENGTH: 96
<212> TYPE: RNA
<213> ORGANISM: Homo sapiens

<400> SEQUENCE: 5
acauugcuac uuacaauuag uuuugcaggu uugcauuuca gcguauauau guauaugugg      60
cugugcaaau ccaugcaaaa cugauuguga uaaugu                               96

<210> SEQ ID NO 6
<211> LENGTH: 23
<212> TYPE: RNA
<213> ORGANISM: Homo sapiens

<400> SEQUENCE: 6
caaagugcuu acagugcagg uag                                             23

<210> SEQ ID NO 7
<211> LENGTH: 84
<212> TYPE: RNA
<213> ORGANISM: Homo sapiens

<400> SEQUENCE: 7
gucagaauaa ugucaaagug cuuacagugc agguagugau augugcaucu acugcaguga     60
aggcacuugu agcauuaugg ugac                                            84

<210> SEQ ID NO 8
<211> LENGTH: 23
<212> TYPE: RNA
<213> ORGANISM: Homo sapiens

<400> SEQUENCE: 8
uaaggugcau cuagugcaga uag                                             23

<210> SEQ ID NO 9
<211> LENGTH: 71
<212> TYPE: RNA
<213> ORGANISM: Homo sapiens

<400> SEQUENCE: 9
uguucuaagg ugcaucuagu gcagauagug aaguagauua gcaucuacug cccuaagugc     60
uccuucuggc a                                                          71

<210> SEQ ID NO 10
<211> LENGTH: 23
<212> TYPE: RNA
<213> ORGANISM: Homo sapiens

<400> SEQUENCE: 10
uaaagugcuu auagugcagg uag                                             23

<210> SEQ ID NO 11
<211> LENGTH: 71
<212> TYPE: RNA
<213> ORGANISM: Homo sapiens

<400> SEQUENCE: 11
guagcacuaa agugcuuaua gugcagguag uguuuaguua ucuacugcau uaugagcacu     60
uaaaguacug c                                                          71
```

```
<210> SEQ ID NO 12
<211> LENGTH: 22
<212> TYPE: RNA
<213> ORGANISM: Homo sapiens

<400> SEQUENCE: 12
uauugcacuu gucccggccu gu                                                   22

<210> SEQ ID NO 13
<211> LENGTH: 78
<212> TYPE: RNA
<213> ORGANISM: Homo sapiens

<400> SEQUENCE: 13
cuuucuacac agguugggau cgguugcaau gcuguguuuc uguaugguau ugcacuuguc          60
ccggccuguu gaguuugg                                                        78

<210> SEQ ID NO 14
<211> LENGTH: 75
<212> TYPE: RNA
<213> ORGANISM: Homo sapiens

<400> SEQUENCE: 14
ucaucccugg gugggauuu guugcauuac uuguguucua uauaaaguau ugcacuuguc           60
ccggccugug gaaga                                                           75

<210> SEQ ID NO 15
<211> LENGTH: 6
<212> TYPE: RNA
<213> ORGANISM: Homo sapiens

<400> SEQUENCE: 15 aaagug                                                                     6

<210> SEQ ID NO 16
<211> LENGTH: 6
<212> TYPE: RNA
<213> ORGANISM: Homo sapiens

<400> SEQUENCE: 16 aaagug                                                                     6

<210> SEQ ID NO 17
<211> LENGTH: 6
<212> TYPE: RNA
<213> ORGANISM: Homo sapiens

<400> SEQUENCE: 17 aaggug                                                                     6

<210> SEQ ID NO 18
<211> LENGTH: 6
<212> TYPE: RNA
<213> ORGANISM: Homo sapiens

<400> SEQUENCE: 18 gugcaa                                                                     6

<210> SEQ ID NO 19
<211> LENGTH: 6
<212> TYPE: RNA
<213> ORGANISM: Homo sapiens
```

```
<400> SEQUENCE: 19 gugcaa                                                                  6

<210> SEQ ID NO 20
<211> LENGTH: 6
<212> TYPE: RNA
<213> ORGANISM: Homo sapiens

<400> SEQUENCE: 20 auugca                                                                  6
```